US009683946B2

(12) United States Patent
Otani et al.

(10) Patent No.: US 9,683,946 B2
(45) Date of Patent: Jun. 20, 2017

(54) METHOD AND DEVICE FOR DETECTING DEFECTS AND METHOD AND DEVICE FOR OBSERVING DEFECTS

(71) Applicant: Hitachi High-Technologies Corporation, Minato-ku, Tokyo (JP)

(72) Inventors: Yuko Otani, Tokyo (JE); Taketo Ueno, Tokyo (JP); Hideki Nakayama, Tokyo (JP); Toshifumi Honda, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 77 days.

(21) Appl. No.: 14/441,742

(22) PCT Filed: Nov. 5, 2013

(86) PCT No.: PCT/JP2013/079902
§ 371 (c)(1),
(2) Date: May 8, 2015

(87) PCT Pub. No.: WO2014/073532
PCT Pub. Date: May 15, 2014

(65) Prior Publication Data
US 2015/0276622 A1     Oct. 1, 2015

(30) Foreign Application Priority Data

Nov. 8, 2012  (JP) ................................ 2012-246035

(51) Int. Cl.
*G01N 21/95*     (2006.01)
(52) U.S. Cl.
CPC .............................. *G01N 21/9501* (2013.01)
(58) Field of Classification Search
CPC ............. G01N 21/9501; G01N 21/956; G01N 2021/1765; G01N 2021/06113; G01N 21/47; G01N 21/21; G01N 21/94
See application file for complete search history.

(56) References Cited

U.S. PATENT DOCUMENTS 4,168,438 A * 9/1979 Morisue ............... G08B 17/113
                                                        250/574
4,642,803 A * 2/1987 Drexler .................... G11B 7/08
                                                        250/208.5
(Continued)

FOREIGN PATENT DOCUMENTS

JP      2000-352697 A     12/2000
JP      2001-133417 A     5/2001
(Continued)

OTHER PUBLICATIONS

English translation of Office Action for related Japanese Patent Application No. 2012-246035 (mailed Nov. 4, 2015).
(Continued)

*Primary Examiner* — Sang Nguyen
(74) *Attorney, Agent, or Firm* — Miles & Stockbridge P.C.

(57) ABSTRACT

The present invention is suppressing the elongating phenomenon in the dark field image of defects in detecting a minute defect by using a dark field microscope. Provided is a method for detecting defects in which scattered light generated from the sample, is concentrated to form an image and is captured and processed to extract a defect to find the positional information of the defect, and the positional information is output, wherein an image of the scattered light that suppresses the occurrence of the elongating phenomenon is formed for which partial shielding of a component of the forward scattered light, that passes through a region near the outer edge of the field of view of the objective lens, and the positional information for the defect is found from a luminance signal for a defect that is extracted from a captured scattered light image that suppresses the occurrence of the elongating phenomenon.

6 Claims, 19 Drawing Sheets

(56) References Cited

U.S. PATENT DOCUMENTS

| | | | |
|---|---|---|---|
| 6,407,373 B1 | 6/2002 | Dotan | |
| 7,719,673 B2 | 5/2010 | Oshima et al. | |
| 8,638,429 B2* | 1/2014 | Nakao | G01N 21/8806 356/237.2 |
| 8,922,764 B2* | 12/2014 | Urano | G01N 21/956 356/237.1 |
| 8,953,156 B2 | 2/2015 | Otani et al. | |
| 2006/0066844 A1 | 3/2006 | Moribe et al. | |
| 2008/0144023 A1 | 6/2008 | Shibata et al. | |
| 2009/0002695 A1* | 1/2009 | Saito | G01N 21/8806 356/237.4 |
| 2012/0274931 A1* | 11/2012 | Otani | G01N 21/21 356/237.3 |

FOREIGN PATENT DOCUMENTS

| | | |
|---|---|---|
| JP | 2006-090728 A | 4/2006 |
| JP | 2008-116405 A | 5/2008 |
| JP | 2008-157638 A | 7/2008 |
| JP | 2011-106974 A | 6/2011 |
| KR | 2006-0051434 A | 5/2006 |

OTHER PUBLICATIONS

Office Action dated Oct. 21, 2016 for related Korean Patent Application No. 10-2015-7010239.

\* cited by examiner

F I G. 1
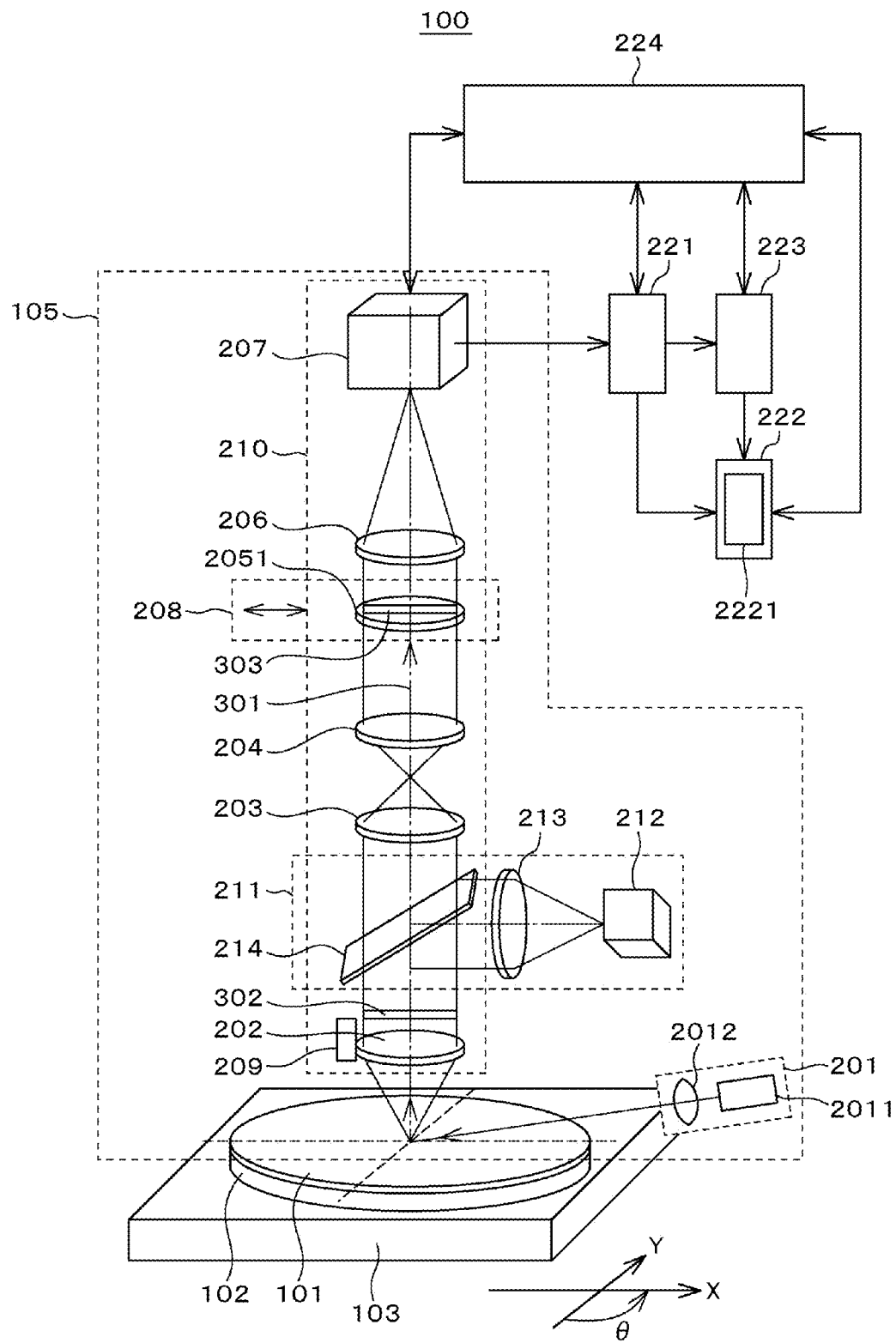

FIG. 2
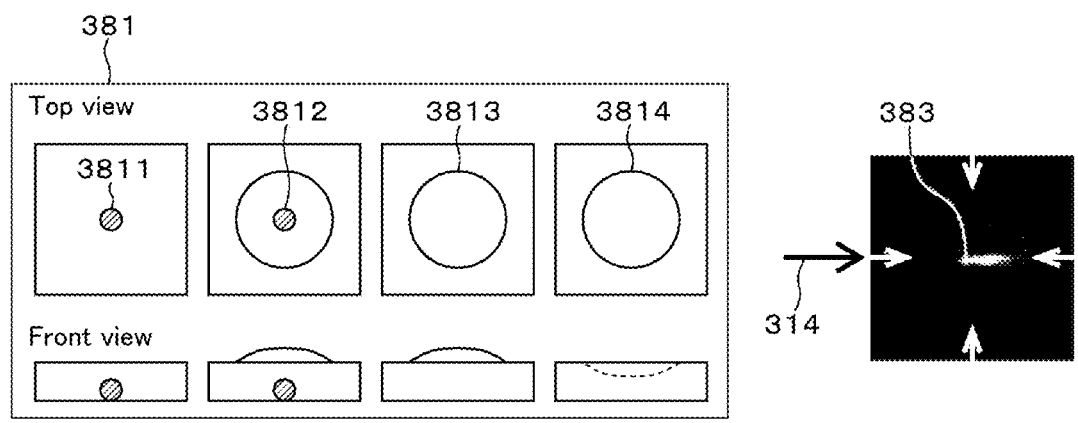
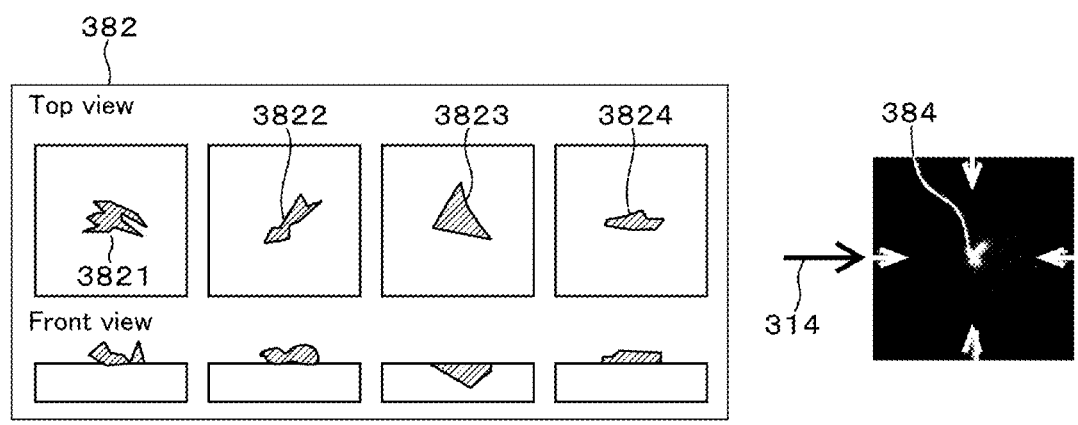

F I G. 5
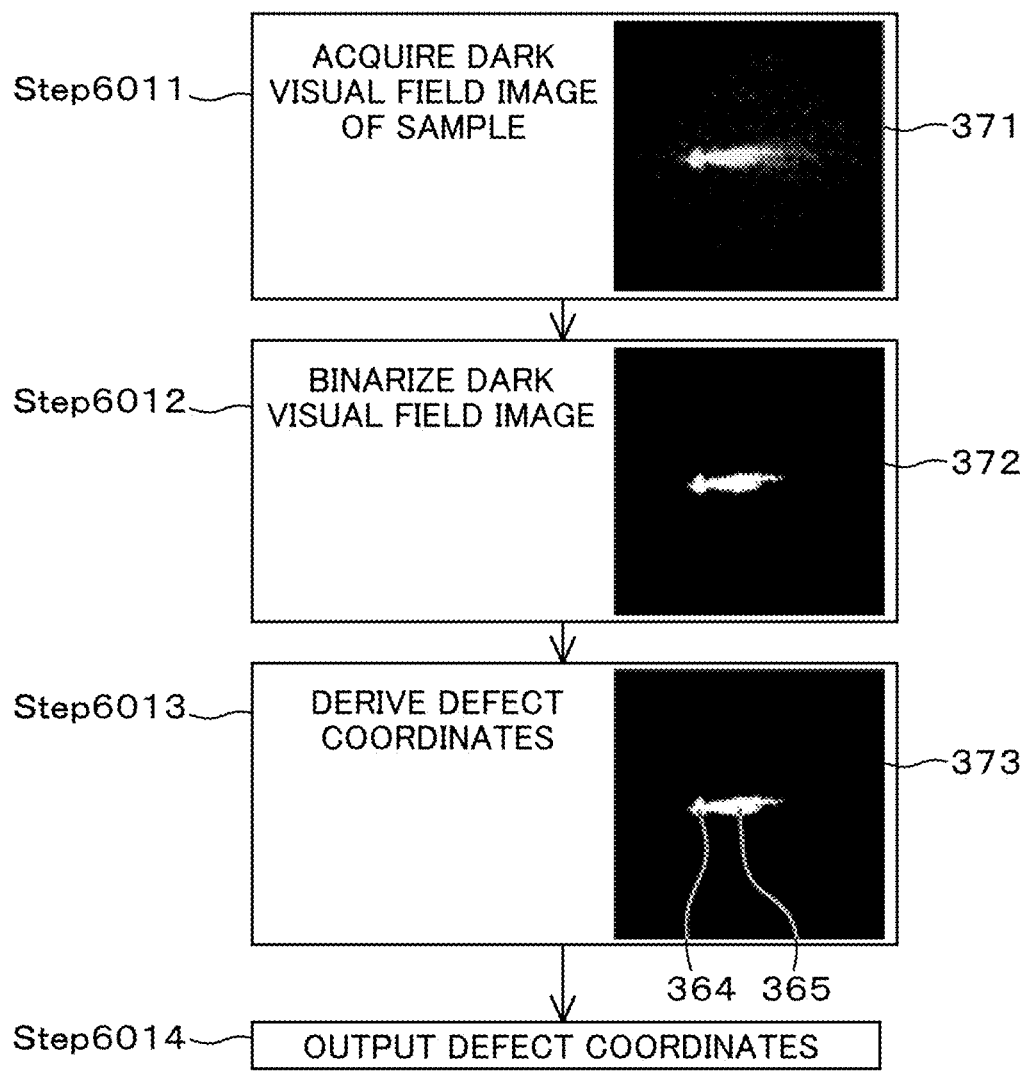

F I G. 1 2
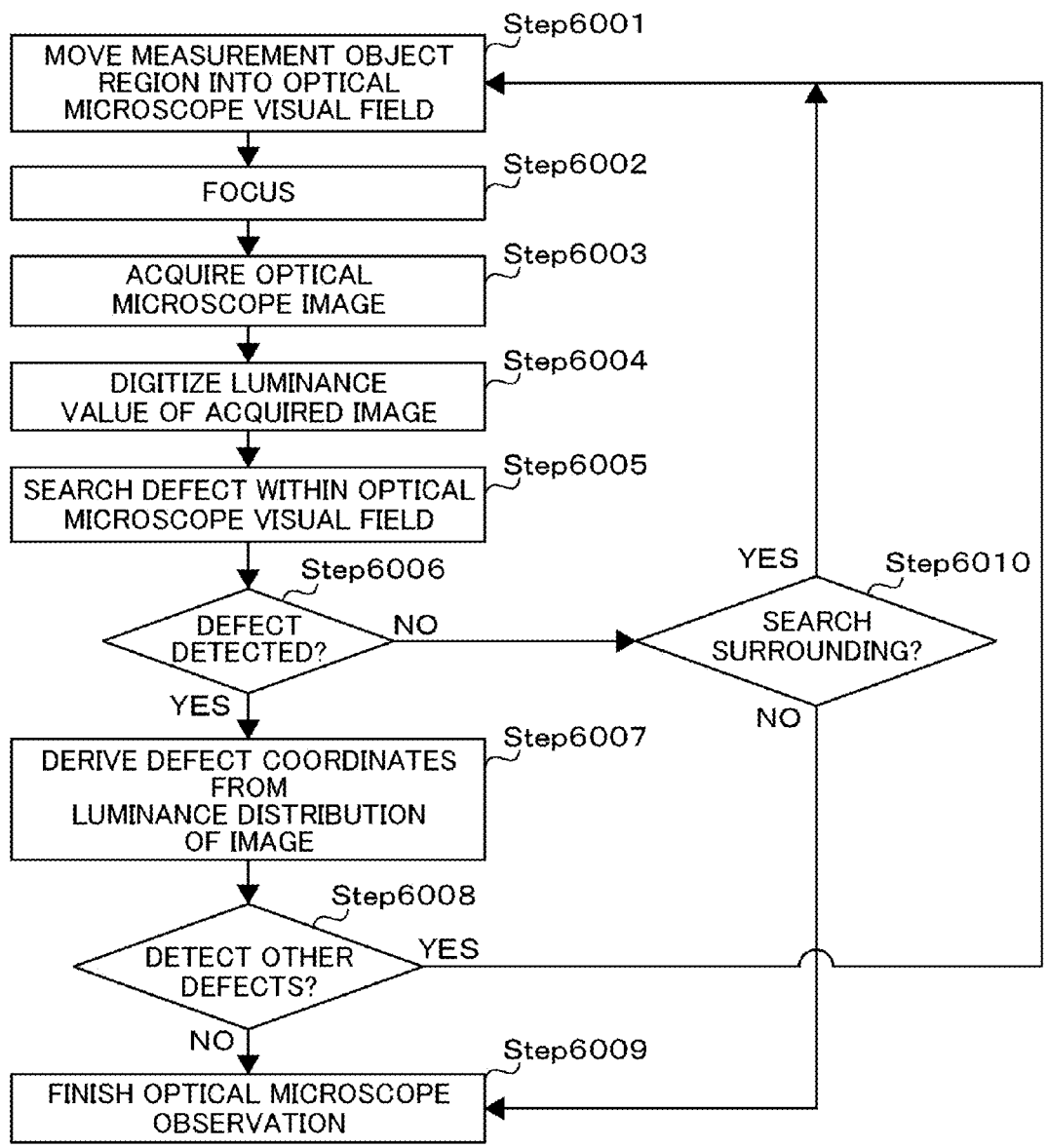

F I G. 1 5 A
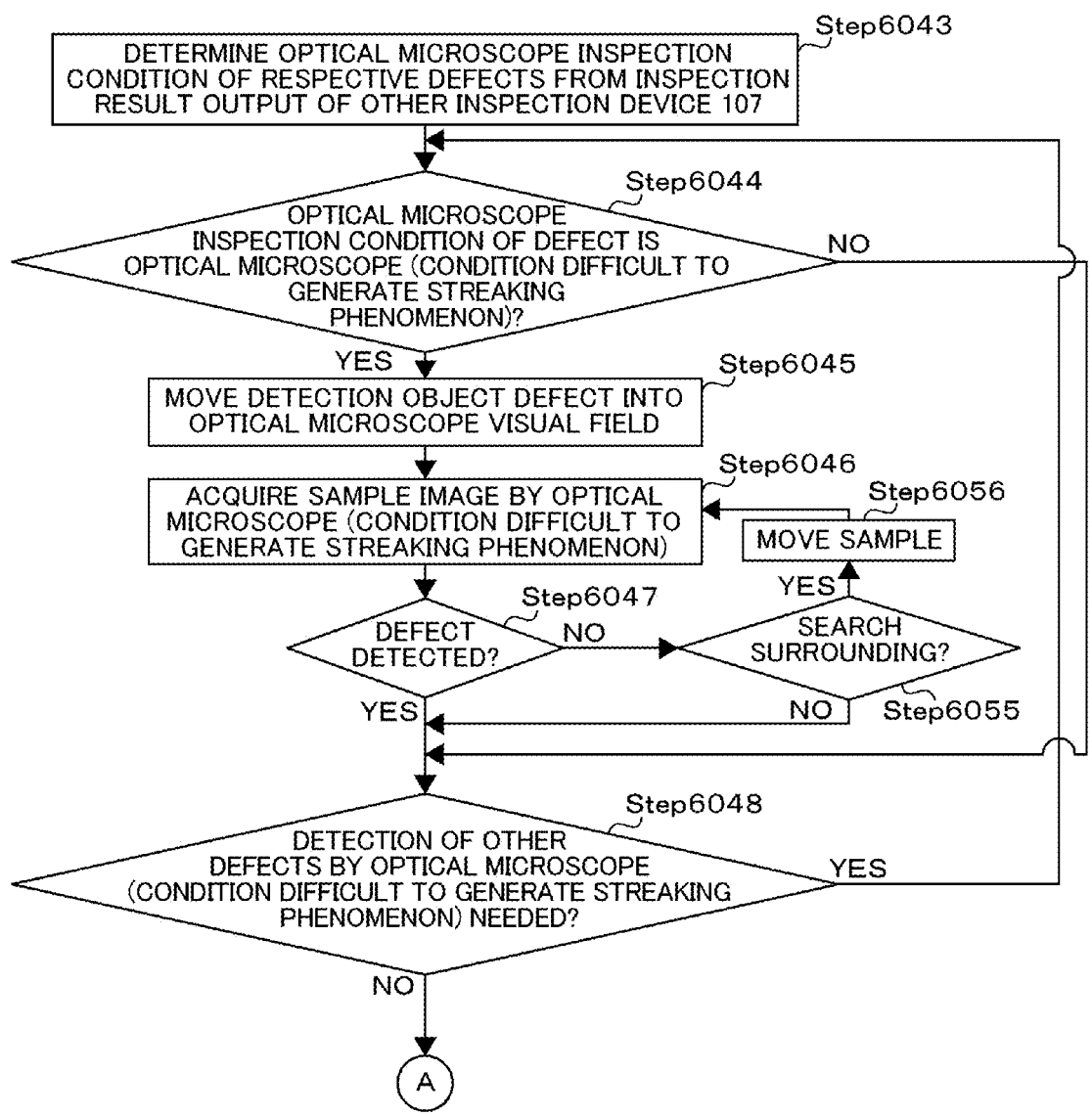

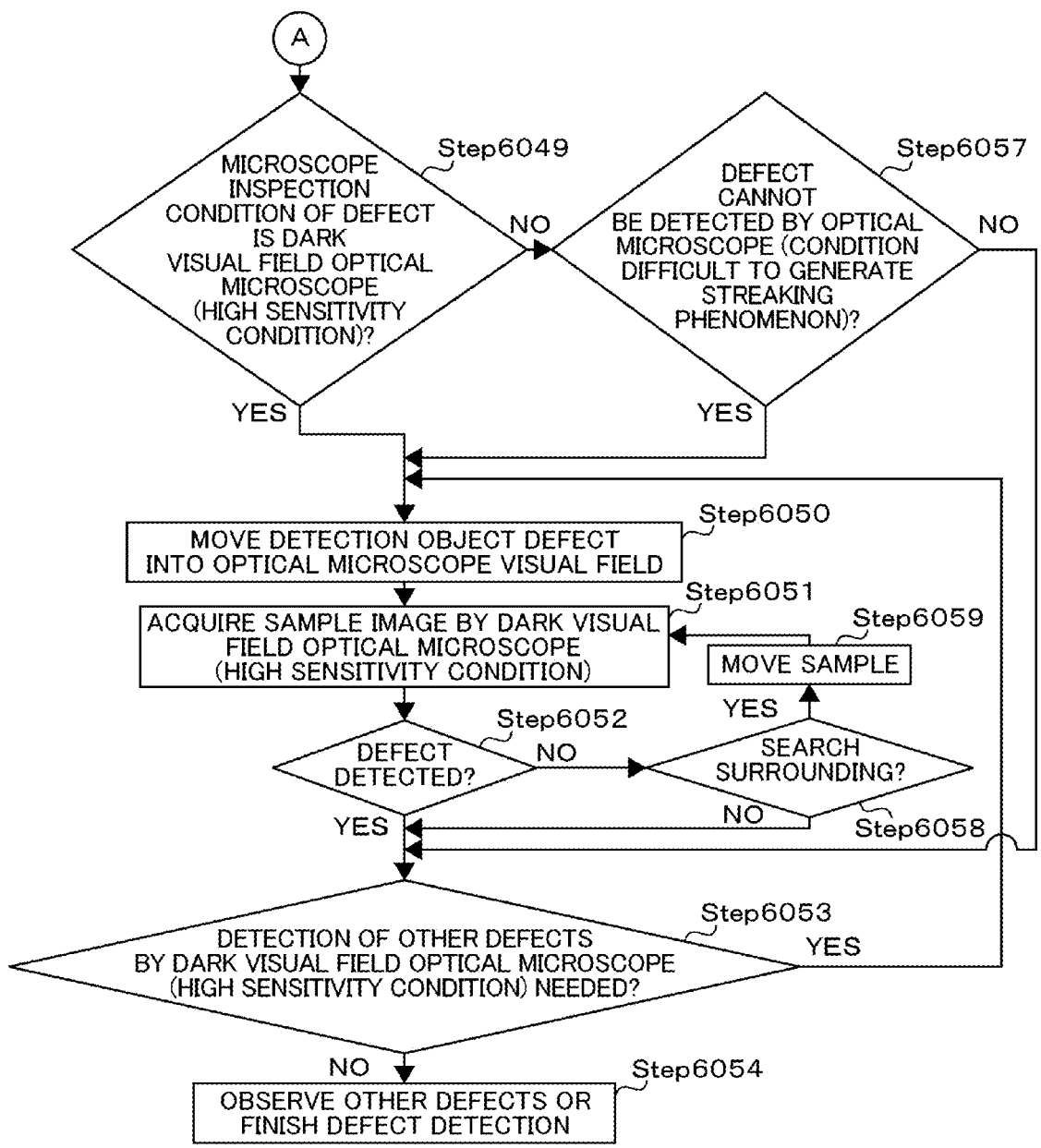
F I G. 15B

US 9,683,946 B2

METHOD AND DEVICE FOR DETECTING DEFECTS AND METHOD AND DEVICE FOR OBSERVING DEFECTS

TECHNICAL FIELD

The present invention relates to a method and a device for detecting defects enabling to highly accurately detect a position of a minute defect which occurs on a semiconductor wafer and a method and a device of observing defects for observing a defect detected by other inspection device by using the device for detecting defects in steps of fabricating a semiconductor device.

BACKGROUND ART

For example, in fabricating steps of a semiconductor device, when a foreign matter or a pattern defect of short circuit, disconnection or the like (hereinafter, these are generally described as defects) is present on a semiconductor substrate (wafer), the defect causes a failure of insulation failure, short circuit or the like of wirings. Also, in accordance with miniaturization of a circuit pattern formed on a wafer, a minute defect causes insulation failure of a capacitor or breakage of a gate oxide film or the like. These defects are mixed in various states by various causes such as those that occur from a movable portion of a carrier device, those generated from the human body, those generated by a reaction at an inner portion of a processing device by a process gas, and those mixed into a drug or a material or the like. Therefore, it is important for mass-producing a semiconductor device to detect a defect generated in fabrication steps, swiftly find a source of generating the defect, and stop creating a failure.

Up to now, as a method of pursuing a cause of generating a defect, there has been a method of first, specifying a defect position by a defect inspecting device, observing in details and classifying the defect by a review device of a scanning electron microscope (SEM) or the like, comparing inspection results acquired at respective steps of fabrication with preserved database to thereby estimate a cause of generating a defect.

Here, the defect inspecting device is an optical defect inspecting device of irradiating a surface of a semiconductor substrate with a laser, subjecting scattered light from the defect to a dark field observation to thereby specify a position of a defect, or an optical outlook inspecting device or an SEM type inspecting device of defecting a bright visual field optical image of a semiconductor substrate by irradiating a semiconductor substrate with a lamp or a laser, or an electron beam, and comparing the bright visual field optical image with reference information to thereby specify a position of a defect on a semiconductor substrate. Such observation methods are disclosed in Patent Literature 1 or Patent Literature 2.

Also, concerning a device of observing in details a defect by SEM, Patent Literature 3 describes a method and a device of detecting a position of a defect on a sample by an optical microscope mounted to an SEM type defect observing device by using position information of the defect on the sample detected by other inspecting device, modifying the position information of the defect acquired by detecting by the other inspecting device, and thereafter, observing (reviewing) in details the defect by the SEM type defect observing device.

Further, Patent Literature 4 describes high sensitivity formation of a dark visual field type optical microscope by arranging a spatially distributed filter on a pupil surface of a detecting optical system or vicinity thereof.

CITATION LIST

Patent Literature

Patent Literature 1: Japanese Unexamined Patent Application Publication No. 2000-352697
Patent Literature 2: Japanese Unexamined Patent Application Publication No. 2008-157638
Patent Literature 3: U.S. Pat. No. 6,407,373
Patent Literature 4: Japanese Unexamined Patent Application Publication No. 2011-106974

SUMMARY OF INVENTION

Technical Problem

In LSI fabrication in recent years, a size of a defect which affects adverse influence on a performance of a device is also miniaturized by miniaturizing a circuit pattern in correspondence with needs of highly integrated formation. In correspondence therewith, miniaturization of a defect dimension to be detected by an optical defect inspecting device is requested. Under such a circumstance, high NA formation (NA: Numerical Aperture) of the inspection optical system is carried out for improving a sensitivity of an inspecting device. A resolution of the detection optical system is inversely proportional to NA. Also, the larger the NA, the more scattered light from a detection object defect can be captured. Therefore, the detection optical system of high NA is effective for high sensitivity formation of detecting a defect. However, in a case of a dark visual field optical microscope having a detection optical system of high NA, a problem is posed that in a defect scattered by being concentrated spatially locally, a dark visual field image of the defect is not focused to a point but is streaked as in a comet (hereinafter, referred to as elongating phenomenon). In a case of deriving coordinates of the defect from the dark visual field image of the defect, accuracy of the coordinates of the defect derived is reduced by a streak produced by the elongating phenomenon. Also, it poses a problem of giving an observer the impression that the defect shape is significantly different from an inherent defect shape.

It is not described to suppress the elongating phenomenon of the dark visual field image of the defect generated when a minute defect is detected by using a dark visual field microscope in any of Patent Literatures 1 through 4 described above.

Hence, the present invention provides a method and a device of detecting a defect as well as a method and a device of observing a defect which suppress an occurrence of a elongating phenomenon by resolving the problem of the background art.

Solution to Problem

To resolve the problem described above, an aspect of the present invention is as follows. A defect detecting method comprising the steps of irradiating a sample with a light incident on a surface of the sample from an oblique direction, condensing a scattered light scattered light generated from the sample irradiated with the light and incident on an objective lens to focus an image of the scattered light, acquiring an image by taking the focused image of the scattered light, extracting a defect on the sample by processing the acquired image to calculate position information of the extracted defect, and outputting the calculated position information of the defect, wherein in focusing the image of the scattered light, the image of the scattered light suppressing an occurrence of a elongating phenomenon by the scattered light scattered to a region near to an outer edge portion of an aperture of the objective lens is focused by focusing a light partially shielding a component of the scattered light transmitting a region near to the outer edge portion of the aperture of the objective lens in the scattered light generated at the surface of the sample by irradiating the light in the scattered light incident on the objective lens, and wherein the position information of the extracted defect is calculated based on a luminance signal of the defect extracted from the image acquired by taking the image of the scattered light suppressing the occurrence of the elongating phenomenon by the scattered light scattered to the region near to the outer edge portion of the aperture of the objective lens.

To resolve the problem described above, an aspect of the present invention is as follows. A defect detecting device comprising mounting stage which mounts a sample, illuminating unit which irradiates the sample by making a light incident on a surface of the sample mounted on the mounting unit from an oblique direction, image taking unit including an objective lens which condenses a scattered light generated from the sample irradiated with the light by the illuminating unit, a focusing lens for focusing an image of the scattered light condensed by the objective lens, and an image taking element for taking an image of the scattered light focused by the focusing lens, image processing unit which extracts a defect on the sample by processing an image of the scattered light provided by taking the image of the scattered light by the image taking unit, and calculating position information of the extracted defect, and outputting unit which outputs the position information of the defect calculated by the image processing unit, wherein the image taking unit further includes a filter for partially shielding a scattered light scattered to a region near to an outer edge portion of an aperture of the objective lens in the scattered light incident on the objective lens, an image of the scattered light suppressing an occurrence of a elongating phenomenon by the scattered light scattered to the region near to the outer edge portion of the aperture of the objective lens is focused by focusing the scattered light transmitted through the filter by the focusing lens, and an image of the scattered light focused and suppressing the occurrence of the elongating phenomenon is taken by the image taking element, and wherein the image processing unit calculates the position information of the defect based on a luminance signal of the defect extracted from the image acquired by taking the image of the scattered light suppressing the occurrence of the elongating phenomenon.

To resolve the problem described above, an aspect of the present invention is as follows. A defect observing method comprising the steps of taking an image of a scattered light generated from a sample by irradiating a light to the sample mounted on a stage by using position information of a defect on the sample detected by another inspection device, calculating position information of the defect mounted on the stage by processing the image of the scattered light provided by taking the image, modifying the position information of the defect on the sample detected by the other inspection device by using the calculated position information on the stage of the defect, and observing the defect detected by the other inspection device on the sample mounted on the stage by using the modified position information, wherein the image of the scattered light is taken by irradiating the sample with a light from an oblique direction to a surface of the sample which is mounted on the stage and in which the defect is detected by the other inspection device, focusing an image of the scattered light suppressing an occurrence of a elongating phenomenon by a scattered light scattered to a region near to an outer edge portion of the aperture of the objective lens by focusing a scattered light partially shielding a component of the scattered light transmitting the region near to the outer edge portion of the aperture of the objective lens in the scattered light generated at the surface of the sample by irradiating the light in the scattered light incident on the objective lens, scattered light light elongating scattered light scattered light acquiring the image suppressing the occurrence of the elongating phenomenon by the scattered light by taking the image of the focused scattered light, scattered light elongating scattered light the position information of the defect on the stage is calculated by extracting the defect on the sample by processing the image suppressing the occurrence of the elongating phenomenon by the acquired scattered light, and calculating the position information of the extracted defect based on a luminance signal of the extracted defect from the image of the scattered light suppressing the elongating phenomenon by the scattered light.

To resolve the problem described above, an aspect of the present invention is as follows. A defect observing method comprising the steps of irradiating a sample mounted on a stage with a light by using position information of a defect on the sample detected by another inspection device and taking an image of a scattered light generated from the sample, calculating the position information of the defect on the stage by processing an image of the scattered light provided by taking the image, modifying the position information of the defect on the sample detected by the other inspection device by using the calculated position information on the stage of the defect, and observing the defect detected by the other inspection device on the sample mounted on the stage by using the modified position information, wherein in the step of taking the image of the scattered light: whether a elongating phenomenon is generated in the taken image of the scattered light is checked, in a case where the elongating phenomenon is generated in the image of the scattered light, irradiating a light to the defect generating the elongating phenomenon from an oblique direction, focusing the image of the scattered light suppressing the occurrence of the elongating phenomenon by the scattered light scattered to the region near to the outer edge position of the aperture of the objective lens scattered light scattered light light light, acquiring the image suppressing the occurrence of the elongating phenomenon by the scattered light by taking the focused image of the scattered light, extracting a defect on the sample by processing the image suppressing the occurrence of the elongating phenomenon by the acquired scattered light, and calculating the position information of the extracted defect based on a luminance signal of the extracted defect.

To resolve the problem described above, an aspect of the present invention is as follows. A defect observing device comprising stage unit which mounts a sample a defect of which is detected by being inspected by another inspection device, image taking unit which takes an image of a scattered light from the sample by irradiating the sample with a light by using position information of the defect on the sample mounted by the stage means, position information extracting unit which calculates position information of the defect detected by detecting the defect from the image of the ray of the scattered light provided by taking an image by the image taking means, defect position information modifying unit which modifies the position information of the defect on the sample detected by the other inspection device by using the position information of the defect calculated by the position information extracting unit, and defect observing unit which observes the defect detected by the other inspection device on the sample by using the position information modified by the defect position information modifying unit, wherein the image taking unit includes an illuminating portion of making a light incident on a surface of the sample which is mounted to the stage unit and in which the defect is detected by the other inspection device from an oblique direction to irradiate the sample, and an image taking portion including an objective lens for condensing a scattered light generated from the sample irradiated with a light by the illuminating portion, a filter partially shielding a scattered light scattered to a region near to an outer edge portion of an aperture of the objective lens in the scattered light condensed by the objective lens, a focusing lens for focusing an image of the scattered light suppressing an occurrence of a elongating phenomenon by focusing the scattered light transmitting through the filter, and an image taking portion including an image taking element of taking an image of the scattered light suppressing the occurrence of the elongating phenomenon focused by the focusing lens, and wherein the position information extracting unit extracts the defect on the sample by processing an image provided by taking the image of the scattered light suppressing an occurrence of the elongating phenomenon at the image taking portion, and calculates the position information of the defect based on a luminance signal of the extracted defect.

Advantageous Effects of Invention

According to the present invention, a minute defect generated on a wafer in fabricating steps of a semiconductor device can be detected with high positional accuracy.

Also, according to the present invention, in a case of observing in details a defect detected by an optical defect detecting device by a review device, a minute defect of an observation object can be put into an observation visual field of SEM or the like, and a throughput of a detailed inspection of the defect using SEM or the like can be improved.

BRIEF DESCRIPTION OF DRAWINGS

FIG. 1 is a block diagram showing an outline configuration of a defect inspecting device according to a first embodiment of the present invention.

FIG. 2 illustrates views showing a relationship between a shape of a defect and a elongating phenomenon.

FIG. 5 illustrates views for explaining cases of reducing a defect coordinates deriving accuracies by the elongating phenomenon.

FIG. 12 is a flowchart of explaining an example of a defect coordinates deriving procedure according to the second embodiment of the present invention.

FIG. 15A is a flowchart of steps from 6028 to 6048 for explaining an example of a procedure of detecting a defect by an optical inspection device according to the second embodiment of the present invention.

FIG. 15B is a flowchart of steps from 6049 to 6058 for explaining an example of a procedure of detecting a defect by an optical inspection device according to the second embodiment of the present invention.

DESCRIPTION OF EMBODIMENTS

Figure 3A:
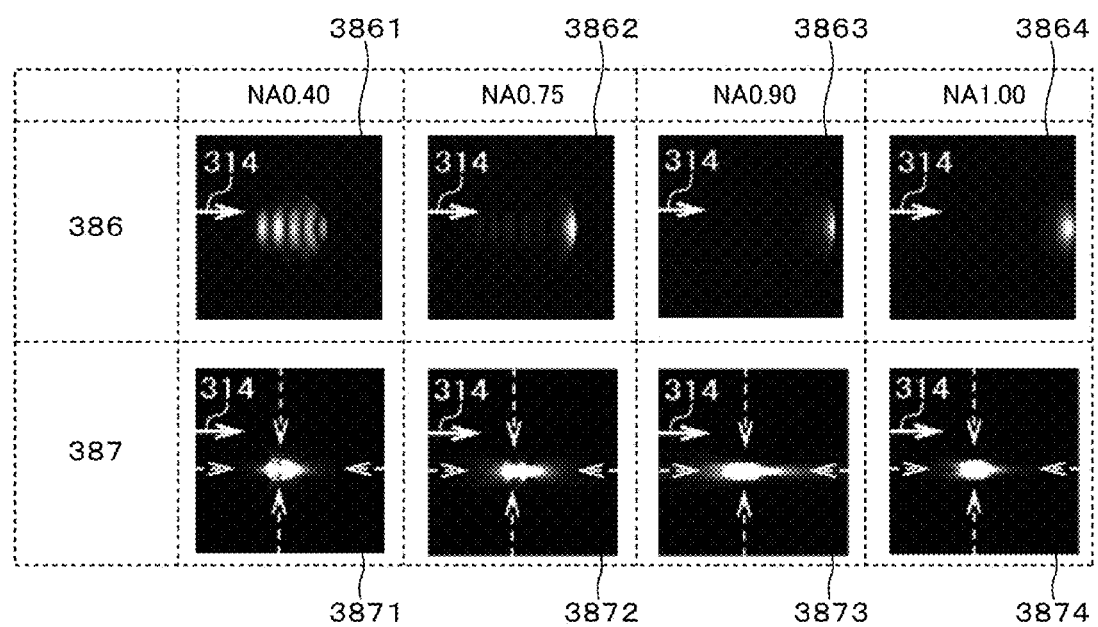
FIG. 3A illustrates views of showing a relationship between NA of a detection optical system and a dark visual field image of defects.

The present invention relates to a method and a device of detecting a defect enabling to make detection of a minute defect at high speed and accurate detection of a position of the minute defect compatible with each other and a method and a device of observing a defect detected by another inspection device by using the defect detecting device.

Embodiments of the present invention will be explained in reference to the drawings as follows.

First Embodiment

First, an explanation will be given of an embodiment of a defect detecting device 100 using a dark visual field observation by the optical microscope according to the present invention in reference to FIG. 1.

A defect detecting device 100 according to the present embodiment shown in FIG. 1 is configured by including an optical microscope 105, a signal processing unit 221, an image display unit 222, a signal storing unit 223, and a control unit 224. The control unit 224 is connected to an exterior data processing device by communicating means not illustrated.

The optical microscope 105 is configured by appropriately using an illumination optical system unit 201, an objective lens 202 for sampling scattered light from a sample 101 or subjecting the scattered light to bright visual field observation, a height control mechanism 209 for controlling a height of the objective lens, a half mirror 214 for introducing illumination necessary for bright visual field observation, an illuminating lens 213, a bright visual field light source 212, a focusing optical system 210 for focusing an image of the sample 101 to an imaging element 207 by scattered light sampled by the objective lens 202, the imaging element 207, a signal processing unit 221 for processing a signal obtained by the imaging element 207, an image display unit 222 for displaying a signal provided by the signal processing unit, and a signal storing unit 223 for preserving a signal provided by the signal processing unit. In addition, the focusing optical system 210 is configured by appropriately including a spatially distributed optical element (filter) 205 and a spatially distributed optical element switching mechanism (filter holder) 208.

The bright visual field light source 212 can use a lamp or a laser. In a case of using a laser, an illumination lens 213 may not be present, illumination can be made bright and more scattered light can be guided to the imaging element 207 by exchanging the half mirror 214 with a dichroic mirror.

A ratio of reflection to transmission of the half mirror 214 may be arbitrarily. However, in a case of sufficiently ensuring an optical intensity of the bright visual field light source, it is preferable to construct a configuration of guiding more scattered light from a defect to the focusing optical system 210 and the imaging element 207, and in a case where the bright visual field illuminating unit is not used as movable type, the bright visual field illuminating unit may be detached from an optical axis 301. In that case, there is an advantage of capable of guiding more scattered light to the imaging element 207.

An illumination optical system unit 201 is configured by appropriately using a light source 2011, and a condensing lens 2012 for concentratedly illuminating a light ray irradiated from the light source 2011 onto the sample 101.

As a configuration of the height control mechanism 209, a configuration of moving by using, for example, a piezoelectric element, a configuration of moving in Z direction (a direction along an optical axis 301 of the focusing optical system 210), along a linear guide by using a stepping motor and a ball screw, or a configuration of moving in Z direction along a linear guide by using an ultrasonic motor and a ball screw or the like can be used.

The imaging element 207 may be arranged at a position conjugated with a sample surface or a position conjugated with a pupil surface of the objective lens.

The focusing optical system 210 is configured by appropriately using lenses 203 and 204 of taking out a pupil surface 302 of the objective lens 202, a focusing lens 206 for focusing an image of the sample 101 onto the imaging element 207, and a filter 205 inserted to the pupil surface 303 of the objective lens 202 taken out by the lenses 203 and 204 or a vicinity of the pupil surface 303.

According to the present embodiment, there is constructed a configuration of inserting a filter holder 208 holding the plural filters 205 having different properties and capable of switching the filters 205 to the pupil surface 303 or the vicinity of the pupil surface. Also, the filter 205 may not be arranged on the optical axis 301 of the focusing optical system 210. Further, the imaging element 207 is connected to the image processing unit 221. The lenses 203 and 204 are used for drawing the pupil surface 302 of the objective lens 202 to outside to form at an inner portion of the focusing optical system 210.

Further, the filter holder 208 can be driven, and insert the filter 205 selected from the plural filters 205 held by the filter holder 208 onto the pupil surface 303 taken out to the inner portion of the focusing optical system 210.

Further, in a case of carrying out bright visual field observation or a case of not using the filter 205, the observation is carried out by setting the position of the filter holder 208 to a location where the filter 205 is not installed for avoiding an acquired image from being disturbed. Or, the filter holder 208 is switched to a location of installing a parallel flat plate glass having a thickness the same as that of the filter 205 to the filter holder 208. The parallel flat plate glass having the thickness the same as that of the filter 205 is installed for avoiding that when the filter 205 is detached, the optical path length is changed, and the image of the sample 101 is not focused onto the imaging element 207. Or, a mechanism may be used in which the parallel flat plate glass is not installed, a position of the focusing lens 206 or the imaging element 207 for focusing an image is adjusted, and the image is focused onto the imaging element 207.

According to the present embodiment, the image of the sample 101 is respectively focused onto a detection face of the imaging element 207 by one set of 4 pieces of the objective lens 202, the lenses 203 and 204, and the lens 206. Although according to the present embodiment, the focusing optical system 210 uses two sheets of lenses of the lenses 203, and 204 other than the objective lens 202 and the focusing lens 206, one of the lenses 203 and 204 will do, and can appropriately be selected.

According to the present embodiment, in the configuration shown in FIG. 1, the pupil surface 302 of the objective lens 202 is focused onto the pupil surface 303 by using the lenses 203 and 204. However, in a case of using the objective lens 202 capable of arranging the filter at the pupil surface 302, or in a case of using a filter which is not necessary to be arranged at the pupil surface 302, or the pupil surface 303, or vicinities of the pupil surfaces for the filter 205 as in detecting linearly polarized light, the image may be focused onto the imaging element 207 by using the objective lens 202 and the focusing lens 206 without using the lenses 203 and 204.

Next, an explanation will be given of the elongating phenomenon that is generated in the detection optical system of high NA in reference to FIG. 2 through FIG. 4.

In LSI fabrication in recent years, by miniaturization of the circuit pattern in correspondence with the needs of the highly integrated formation, also the size of the defect which affects adverse influence on the performance of the device is miniaturized. In correspondence therewith, miniaturization of a defect dimension to be detected by the optical defect inspecting device is requested, and the detection optical system of high NA is adopted in an inspection device for improving a detection sensitivity of a defect. This is because the resolution of the detection optical system is inversely proportional to NA and the larger the NA, the more scattered light from the detection object defect can be captured. However, in a case of a dark visual field observation by the optical microscope having the detection optical system of high NA, in a defect scattered by being locally concentrated spatially, a dark visual field image of the defect is not focused to a point but the elongating phenomenon of elongating like a comet is brought about, and in a case of deriving the defect coordinates from the dark visual field image of the defect, the derived defect coordinates accuracy is reduced by a streak produced by the elongating phenomenon. Further, it poses a problem of giving an observer the impression that the defect shape is significantly different from an inherent defect shape.

Next, an explanation will be given of the elongating phenomenon of an optical microscope image produced at a portion of defects in reference to FIG. 2.

The elongating phenomenon of the optical microscope image indicates a phenomenon of producing a defect streaked to be long different from an actual defect shape. In defects 3811 through 3814 having substantially isotropic shapes when viewed from a top side (Top view) and viewed from a front side (Front view) as shown in a defect example 381 of FIG. 2(a), as shown in an example 383 of a dark visual field image of the defect, there is the elongating phenomenon of extending a tail in a direction of being extended along an incidence direction 314 of a laser (from left to right in a dark visual field image example 383).

Further, in defect examples 3821 through 3824 which are not isotropic when viewed from a top side (Top view) and viewed from a front side (Front view) as shown in a defect example 382 of FIG. 2(b), as shown in a dark visual field image example 384 of the defect, there is a elongating phenomenon of extending a tail in a direction that is not related to the incident direction 314 of the laser (in the dark visual field image example 384 from left bottom to right top, from right bottom to left top) as shown in the dark visual field image example 384 of the defect. In the case of the defect example 382, there is also present a defect of extending a tail in a direction of extending from the incidence direction of the laser. Further, in the case of the defect example 382, there is a elongating phenomenon of extending tails in plural directions and a elongating phenomenon of extending a tail in one direction as shown in the dark visual field image example 384.

A defect shape of bringing about the elongating phenomenon is not limited to the defects 3811 through 3814 of the defect example 381 and the defects 3821 through 3824 of the defect example 382, and also the dark visual field image causing the elongating phenomenon is not limited to the examples of dark visual field image 383 and 384.

Figure 3B:
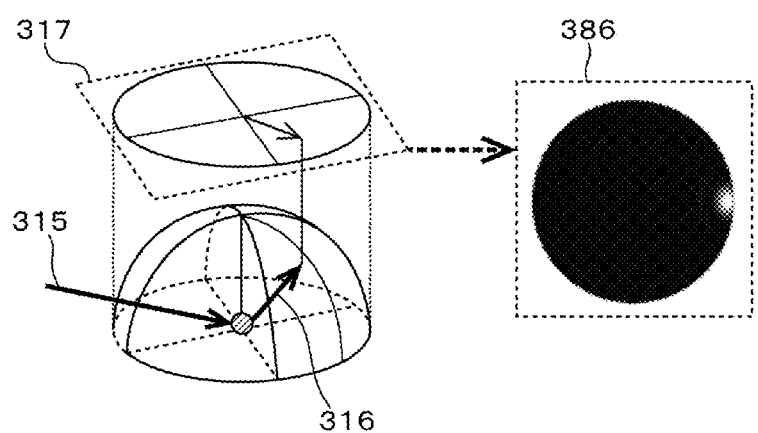
FIG. 3B illustrates a view of a semispherical face showing a state of scattered light generated by a defect illuminated from an inclined direction and a view showing a dark visual field image at that time.
Figure 4:
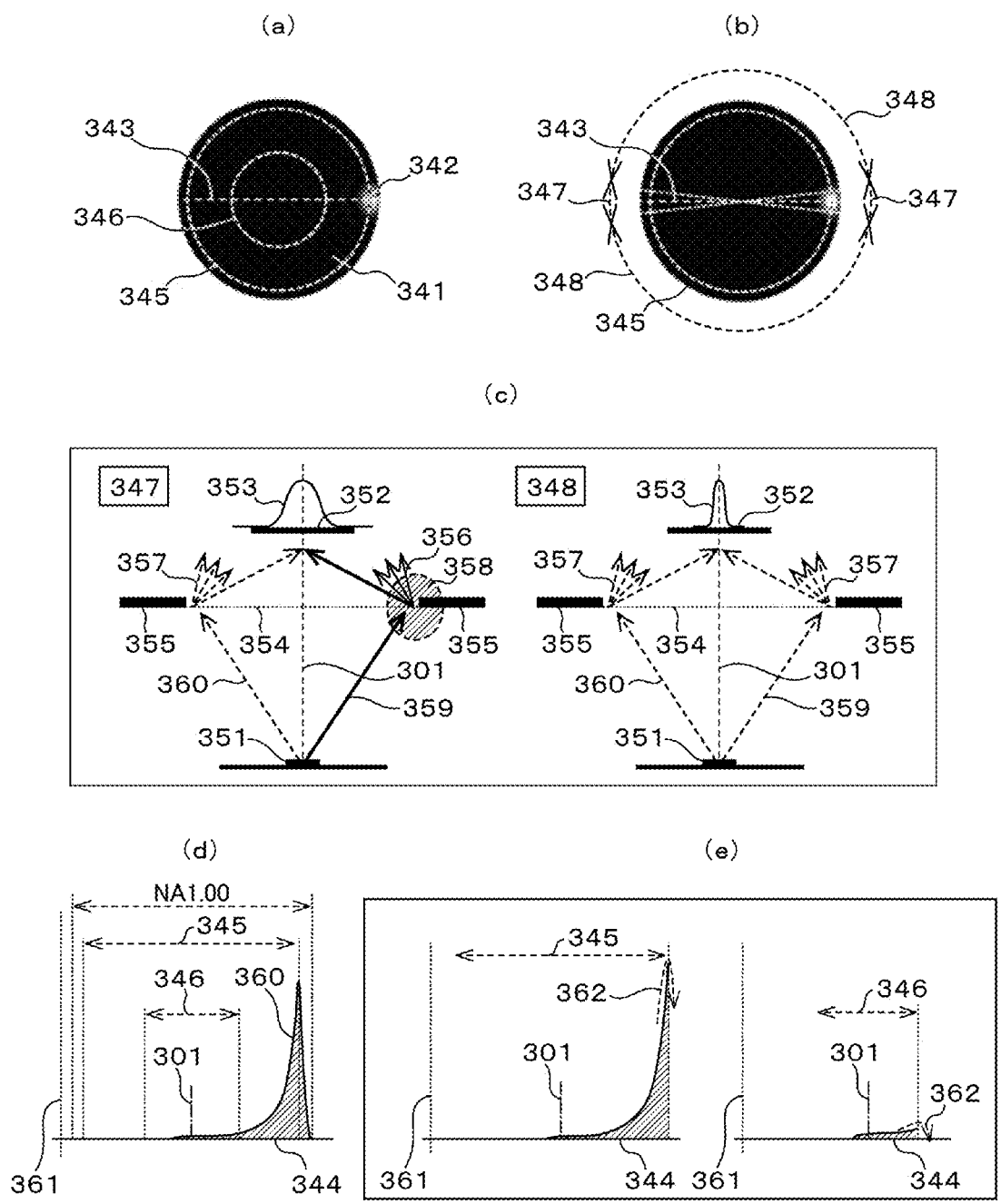
FIG. 4 illustrates views for explaining factors of the elongating phenomenon.

FIG. 3A shows an example of a simulation result of a defect scattered light distribution 386 and a dark visual field image 387 of bringing about the elongating phenomenon in a case where NA of a detection optical system is changed such that 0.40, 0.75, 0.90, 1.00 and using detection optical systems of respective NA's. FIG. 3A shows a result of a defect of extending a tail in a direction along the incidence direction 314 of the laser. The scattered light distribution 386 of the defect shows an intensity distribution of projecting a scattered light intensity distribution on a semispherical face of light 316 at which an illumination light 315 is scattered by the defect onto a two-dimensional face 317 in parallel with the sample face as shown in FIG. 3B.

The respective defect scattered light distributions 3861 through 3864 which are results of a simulation in the defect scattered light distribution 386 shown in FIG. 3A are respectively displayed by relative values. By focusing the defect scattered light distributions 3861 through 3894 in respective NA's, respective dark visual field images 3871 through 3874 are obtained. Real defect center positions are intersection positions of arrows indicating 4 directions from up and down left and right in the respective dark visual field images 3871 through 3874. In the example of the defect shown in FIG. 3A, it is known that the light is scattered locally concentratedly in a low angle region in the forward scattering direction (angle direction near to a normal direction of a surface of the sample 101). As shown in the example of the scattered light distribution 386 of the defect, a defect which is liable to bring about the elongating phenomenon tends to be scattered concentratedly to a local region. Further, it can be confirmed from the dark visual field image 387 that in the defect of FIG. 3A, the elongating phenomenon is brought about in the dark visual field images 3872 and 3873, that is, when NA is 0.75 and 0.90.

Also in an experiment, a result similar to the one of the simulation is obtained. In the detection optical systems of NA 0.60 and 0.75, the elongating phenomenon is brought about at a portion of defects. On the other hand, as shown in the dark visual field image 3871, in the detection optical system of NA 0.40, the elongating phenomenon is not brought about even in the defect of bringing about the elongating phenomenon in the detection optical system of high NA as in NA 0.60 and 0.75. Or, even when the elongating phenomenon is brought about, a length of a tail is significantly shorter than that of the detection optical system of high NA.

There are three causes of generating the elongating phenomenon described below.

(A) Anisotropy of diffracted light intensity at aperture boundary (B) Generation of new light source by projecting scattered light to a vicinity of aperture boundary (C) Rapid change in scattered light intensity at aperture boundary Details of a elongating phenomenon generation mechanism will be explained in reference to FIG. 4 as follows.

FIG. 4(a) shows a scattered light distribution example (NA 1.00) of a elongating defect extending a tail in a direction extended from an incidence direction of a laser. A region 342 is a region having a significantly strong scattered light intensity, and a region 341 is a region having a weak scattered light intensity. A line 343 represents an incidence face of illumination. The incidence face of the illumination light is a face vertical to a sample surface and in parallel with an optical axis of the illumination light, and a face including the optical axis of the illumination light within the face. A circle 345 designates an aperture boundary of NA 0.90, and a circle 346 designates an aperture boundary of NA 0.40, respectively. In a case of FIG. 4(a), in the detection optical system of NA 0.90, an aperture boundary and a region having a strong intensity of defect scattered light overlap each other.

(A) Anisotropy of Diffracted Light Intensity at Aperture Boundary

In a case where the boundary 342 having a strong scattered light intensity and an aperture boundary (in FIG. 4(b), the aperture boundary 345 of NA 0.90) overlap each other, anisotropy of a scattered light intensity at the aperture boundary is enlarged as shown in FIG. 4(b). At a region having a strong scattered light intensity at an aperture boundary, a diffracted light intensity is stronger than that of another region. Light is condensed to the image face, and therefore, a direction of expanding the image is in a direction of an azimuth angle having the strong scattered light intensity, and in a direction of the azimuth angle which is symmetrical with the former azimuth with respect to the optical axis.

In FIG. 4(b), the image is extended in a direction of an azimuth angle having an extremely strong scattered light intensity and an azimuth angle 347 of an azimuth angle symmetrical with the former azimuth angle with respect to the optical axis. On the other hand, at the azimuth angle 348 other than the azimuth angle 347, a diffracted light intensity of scattered light at an aperture boundary is weak, and an expansion of the image is smaller than that in the azimuth angle 347.

In FIG. 4(c), a dotted line 301 designates an optical axis of a detection optical system, numeral 351 designates a scattering body (foreign matter), and an arrow 359 designates strong scattered light, an arrow 360 designates weak scattered light, a line 354 designates a pupil surface, a line 355 designates an aperture boundary, an arrow 356 designates strong diffracted light, an arrow 357 designates weak diffracted light, a line 352 designates an image face, and a line 353 designates an intensity of a dark visual field image, respectively.

(B) Generation of New Light Source by Projecting Scattered Light to Vicinity of Aperture Boundary By overlapping a region having a strong scattered light intensity and the aperture boundary, strong scattered light is irradiated to the aperture boundary, scattered light is reflected or scattered at the aperture boundary, and becomes new light source 358, and generates the elongating phenomenon.

(C) Abrupt Change of Scattered Light Intensity at Aperture Boundary

FIGS. 4(d) and (e) describe the region 342 having a strong scattered light intensity at the aperture boundary, and an intensity change designated by the arrow 360 of scattered light on the line 343 passing the optical axis 301 of the detection optical system in a case where scattered light from a defect is scattered concentratedly to a local area (0 dimension light) of a low angle as in FIG. 4(a). In FIG. 4(d), an abscissa 344 designates a position on an incident face of illumination (line 343 of FIG. 4(a)), an ordinate 361 designates a scattered light intensity, a region 346 designates a detection region of the detection optical system of NA 0.40, and a region 345 designates a detection region of the detection optical system of NA 0.90, respectively. Further, a dotted line 362 of FIG. 4(e) designates an intensity change at an aperture boundary. As is understood also from FIG. 4(a), the wider the aperture, the more significantly the intensity change 362 at the aperture boundary is increased. The larger the intensity, the more light is expanded to outside of the aperture.

Next, a reduction in defect coordinates accuracy by the elongating phenomenon will be described in reference to FIG. 5 by taking an example of the simplest coordinates deriving method by using a dark visual field image. A dark visual field image 371 of an object sample is acquired (Step 6011), the acquired dark visual field image 371 is subjected to a binarization process (Step 6012), a luminance gravity center 365 of the dark visual field image 372 subjected to the binarization process is derived (Step 6013), and the luminance gravity center 365 is outputted as the defect coordinates (Step 6014).

As shown in FIG. 5, separation is brought about between the real coordinates 364 and the defect coordinates 365 outputted by the defect inspecting device. In a case where an amount of the separation is large, when the defect detected by the defect inspecting device is going to be enlarged and observed based on the defect coordinates 365, it is conceivable that the defect is deviated from an observation visual field. Means for suppressing the elongating phenomenon, or means for determining generation of the elongating phenomenon is needed in view of the fact.

The means for suppressing the elongating phenomenon will be described. It is known from the elongating phenomenon generation mechanism explained in reference to FIG. 3 and FIG. 4 that as a method of suppressing the elongating phenomenon, it is effective not to overlap a region having an extremely strong intensity of defect scattered light and the aperture boundary. As a method of suppressing the elongating phenomenon, there is a method of [1] reducing NA of the detection optical system, or [2] making an intensity change at the aperture boundary mild.

As a method of executing the reduction in the detection optical system NA, there is a method of using an objective lens having small NA, or a method of changing a space filter 401 (FIG. 6A) of limiting an aperture at a pupil surface of the detection optical or a vicinity thereof. In a condition of a simulation (illumination incidence angle 80 degrees, visible light), at NA 0.40, an influence of the elongating phenomenon is small, at NA 0.60, the influence of the elongating phenomenon is large, and therefore, it is necessary to limit NA at least equal to or smaller than 0.60 by providing a light shielding region 4012 at a surrounding of a light transmitting region 4011 of the space filter 401. However, an influence degree of the elongating phenomenon is changed by an illumination incidence angle and an illumination wavelength, and therefore, NA necessary for limiting the aperture is not limited thereto.

As a method of making the intensity change at the aperture boundary mild, there is a method of arranging an ND filter (darkening filter) 402 (FIG. 6B) having a transmittance distribution in which a transmittance is gradually changed in a radius direction at the pupil surface of the detection optical system or a vicinity of the pupil surface. The ND filter 402 is provided with a light shielding region 4022 at a surrounding of a light transmitting area 4021 at a center thereof, and the light shielding region 4022 has a spatial distribution in which the transmittance is reduced from the center toward an outer peripheral direction.

Figure 6A:
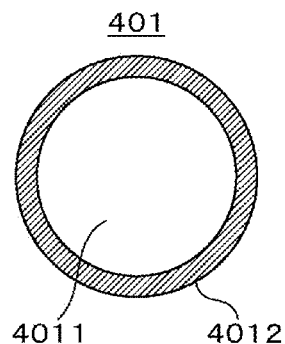
FIG. 6A is a plane view of a filter showing an example of a filter arranged on a pupil surface of a dark visual field optical microscope or vicinity thereof and a plane view of a filter showing an example of being configured by a region of transmitting scattered light and a region of shielding the scattered light.
Figure 6B:
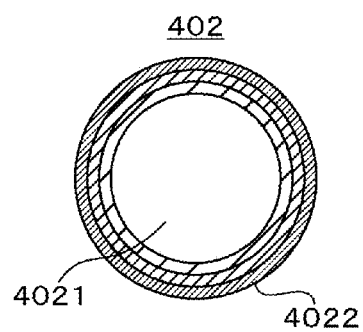
FIG. 6B is a plane view of a filter showing an example of a filter arranged on a pupil surface of a dark visual field optical microscope or vicinity thereof, and an example of being configured by a region of transmitting scattered light and a region of shielding scattered light by gradually reducing a transmittance.

However, according to the method explained in reference to FIG. 6A and FIG. 6B, the defect scattered light is shielded or darkened and defect detection sensitivity is reduced. Therefore, a proper use of detection of a maximum sensitivity and a detection which does not bring about the elongating phenomenon is brought about. This reduces an inspection throughput.

Hence, next, there is a method of using a filter having a partial optical property as means for suppressing the reduction in the defect scattered light as less as possible and suppressing the elongating phenomenon. There is known a tendency where as in the defect example 381 shown in FIG. 2(a), the defect having substantially isotropic shape and elongating phenomenon causes strongly scattered light which is concentrated locally to a vicinity of the low angle region 342 on a front side like the dark visual field image 383, as shown in FIG. 4(a). Hence, there is a method of shielding or darkening only a minimum region for transmitting light scattered on a sample as much as possible.

There is a method of arranging a space filter 403 (FIG. 7A) provided with a region 4032 for shielding a low angle region on a front side in a light transmitting region 4031 at a low angle region on a front side for suppressing the elongating phenomenon concerning the defect concentrated locally at the front low angle region and scattered strongly, or an ND filter 404 (FIG. 7B) provided with a region 4042 having a transmittance distribution in a radius direction at the low angle region on the front side in the light transmission region 4031 at the pupil surface or the vicinity of the pupil surface for making a rapid change in the intensity at a vicinity of the aperture boundary of the low angle region on the front side mild.

Figure 7A:
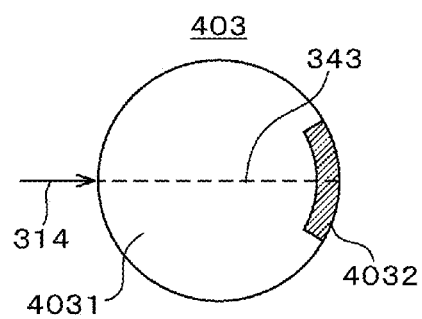
FIG. 7A is a plane view of a filter showing an example of a filter arranged on a pupil surface of a dark visual field optical microscope or a vicinity thereof, and showing an example of being configured by providing a region of shielding forward scattered light at a portion of a region of transmitting scattered light.
Figure 7B:
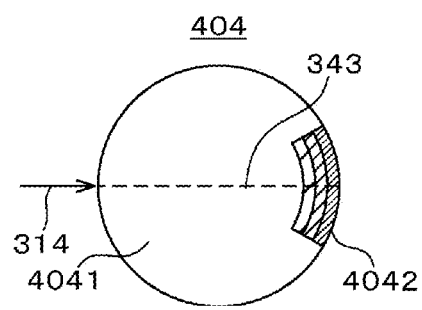
FIG. 7B is a plane view of a filter showing an example of a filter arranged on a pupil surface of a dark visual field optical microscope or a vicinity thereof, and a example of being configured by providing a region of shielding forward scattered light by gradually reducing a transmittance thereof at a portion of a region of transmitting scattered light.

Although scattered light of the wafer is strongly scattered to a rear side, the scattered light is scattered also to a low angle region on a front side, and therefore, in detecting a minute defect of 10-odd nm in size, even when the front low angle region is shielded, an influence of a reduction in sensitivity is small. Therefore, in a case of using the space filter 403 or 404 of FIG. 7A or FIG. 7B, the inspection can be carried out without a proper use of the high sensitivity detection and the elongating phenomenon restraining detection. Also, another filter for detection of high sensitivity formation detection and the detection using a filter having a partial optical characteristic as shown in FIG. 7A or FIG. 7B may properly be used.

As a method of using a filter for high sensitivity detection other than the filter having the partial optical property, there is a method of using a linear polarizer at an arbitrary location of the detection optical system. This is because in a case of P polarization illumination, in a polarization direction of scattered light at a low angle region on a front side, a polarization direction in parallel with an incidence face of illumination is a major component. By arranging a linear polarizer in a direction of shielding polarized light in parallel with an incidence face of illumination, an intensity of scattered light at the front low angle region can be reduced, and the elongating phenomenon can be suppressed.

In a case of using the linear polarizer, there are two advantages. The first advantage is that it is not necessary to arrange the linear polarizer at a vicinity of the pupil surface, but the linear polarizer can be arranged at an arbitrary location of the detection optical system. The second advantage is that in detection using the polarizer, minute defect detection sensitivity is high by suppressing scattered light from the wafer, and therefore, the inspection can be carried out without properly using the high sensitivity detection and the elongating phenomenon suppressing detection. Also, further high sensitivity formation detection and detection using the linear polarizer may properly be used.

Also, the elongating phenomenon is a phenomenon which is remarkably brought about in a dark visual field observation by the optical microscope having laser oblique incidence illumination and a focusing detection optical system of high NA, and therefore, the elongating phenomenon is not brought about in a dark visual field optical microscope of ring illumination of white color or laser light source, a dark visual field optical microscope of white color oblique incidence illumination, a bright visual field optical microscope of white color or laser illumination, a phase contrast microscope, a dark visual field optical microscope having a condensed light detection optical system, SEM or the like. Therefore, as the elongating phenomenon suppressing means, there may be used means which does not bring about the elongating phenomenon of a dark visual field observation by the optical microscope of ring illumination of white color or laser light source, a dark visual field light source for white color oblique incidence illumination, a bright visual field optical microscope of white color or laser illumination, a phase contrast microscope, a dark visual field light source having a condensed light detection optical system, SEM or the like. The dark visual field light source of the white color oblique incidence illumination has an illumination wave length having a width larger than that of the laser, and therefore, a scattered light distribution is not extremely concentrated but is spread, and therefore, the elongating phenomenon is not brought about.

Figure 8A:
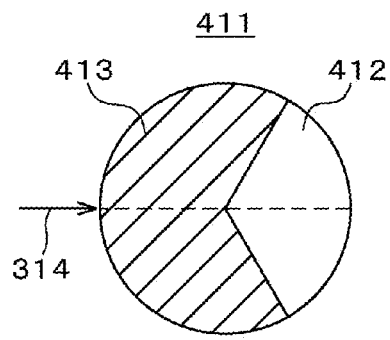
FIG. 8A is a plane view of an example of a filter arranged on a pupil surface of a dark visual field optical microscope or vicinity thereof, and a filter having a configuration of transmitting forward scattered light and shielding another region.
Figure 8B:
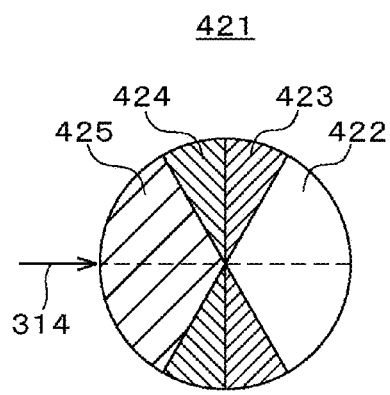
FIG. 8B is a plane view of an example of a filter arranged on a pupil surface of a dark visual field optical microscope or a vicinity thereof, and a filter having a configuration of being provided with a region of transmitting forward scatter light and shielding the other region by gradually reducing a transmittance of scattered light.

Further, as an example of a filter for high sensitivity detection having a partial optical property, there is a filter as shown in FIG. 8A or FIG. 8B. A filter 411 shown in FIG. 8A transmits a forward scattered light component from the sample 101 by a transmitting area 412, and the other scattered light component or stray light is shielded by a shielding portion 413. S/N of a detection signal can be improved, and a smaller defect signal can be detected by using such a filter.

On the other hand, a filter 421 shown in FIG. 4B transmits a forward scattered light component from the sample 101 by a transmitting area 422, and shields the other scattered light component or stray light by light shielding portions 423 through 425 where a transmittance is gradually increased. Even such a filter is used, S/N of a detection signal can be improved similarly to a case of the filter 411 of FIG. 8A, and a smaller defect signal can be detected.

Figure 8C:
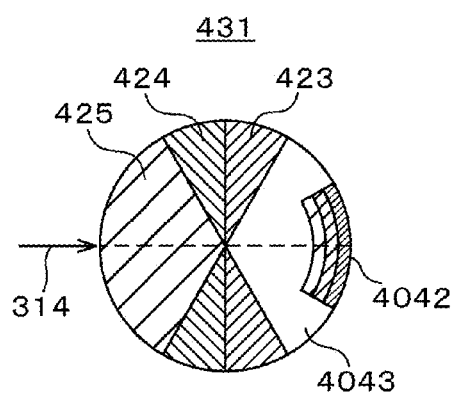
FIG. 8C is a plane view of an example of a filter arranged on a pupil surface of a dark visual field optical microscope or a vicinity thereof, and a filter having a configuration of being provided with a region of shielding forward scattered light by gradually reducing a transmittance thereof at a portion of a region of transmitting scattered light, and a region of transmitting forward scattered light and shielding forward scattered light by gradually reducing a transmittance of scattered light of the other region.

Further, FIG. 8C shows a filter 431 combining the filter 404 shown in FIG. 7B and the filter 421 shown in FIG. 8B. The high sensitivity detection and the detection suppressing the elongating phenomenon can simultaneously be realized by using such filters. A similar effect can also be achieved by combining the filter 403 shown in FIG. 7A, and the filter 411 shown in FIG. 8A.

An explanation will be given of a method of inspecting the sample 101 by using the defect detecting device 100 having the configuration described above.

First, an adjusting method of the focusing optical system 210 will be explained.

For subjecting the sample 101 to bright visual field observation in a state where the sample 101 of the inspection object is mounted a sample holder 102, illumination light is emitted from the bright visual field light source 212, a half of a light amount of illumination light transmitted through the illuminating lens 213 is reflected to a side of the objective lens 202 by the half mirror 214 to be incident on the objective lens 202, and a surface of the sample 101 is subjected to bright visual field illumination. The half of the light amount of the reflected light incident on the objective lens 202 of the light reflected by the sample 101 is condensed by the lenses 203 and 204 by transmitting the half mirror 214, and an image of the surface of the sample 101 is focused on a detection face of the imaging element 207 by the focusing lens 206.

A signal provided by taking the focused image of the surface of the sample 101 by the imaging element 207 is transmitted to the image processing unit 221, and is displayed on a display screen 2221 of the image display unit 222 as an image of the surface of the sample 101.

An operator confirms that the image of the surface of the sample 101 is correctly focused onto the image taking face of the imaging element 207 by observing the bright visual field image of the surface of the sample 101 displayed on the display screen 2221. In a case where the image of the surface of the sample 101 is not correctly focused onto the image taking face of the imaging element 207, a focusing position of the image of the surface of the sample 101 is correctly aligned onto the image taking face of the imaging element 207 by operating a height control mechanism 209 of the objective lens.

Also, the operator confirms whether directions of the sample 101 coincide with X and Y directions which are moving directions of the stage 103, and in a case where the directions are shifted, the operator rotates the stage 103 in θ direction to adjust the directions of the sample 101. The adjustment is carried out before starting inspection, and after finishing the adjustment, the inspection explained below is executed concerning the plural samples 101.

Next, an explanation will be given of a procedure of inspecting the sample 101 in the state of adjusting the focusing optical system 210.

Illumination light is irradiated to the surface of the sample 101 by the illumination optical system unit 201 in a state of mounting the sample 101 of the inspection object on the sample holder 102 (dark visual field illumination). Next, the sample 101 mounted on the sample holder 102 is continuously moved in X direction by a constant speed by controlling to drive the stage 103 movable in X and Y directions within a plane by the control unit 224. In scattered light generated from a region of the surface of the continuously moving sample 101 irradiated with the illumination light by the illumination optical system unit 201, a half of a light amount of scattered light incident on the objective lens 202 is halved by transmitting the half mirror 214, and an image of the scattered light filtered by the filter 205 as the space distribution optical element by transmitting the lenses 203 and 204 is focused onto a detection face (not illustrated) of the imaging element 207 by the focusing lens 206. A signal of taking the image of the scattered light by the imaging element 207 is transmitted to the image processing unit 221, subjected to A/D conversion, thereafter, the signal larger than a threshold is extracted as a defect by a threshold process.

Here, an optical condition of inspection can be switched by switching the filter 205 arranged on the optical axis 301 of the focusing optical system 210 by driving the filter holder 208. The sample 101 can be inspected by plural inspection conditions by inspecting the sample 101 at plural times by switching the filter 205 in this way.

For example, a front face of the sample 101 is inspected by using a filter for suppressing the occurrence of the elongating phenomenon as the filter 205 at a first time inspection for the sample 101, next, the front face of the sample 101 is inspected by switching to a filter suitable for high sensitivity detection as the filter 205 at the second time inspection, thereby, a position of a defect at which the elongating phenomenon is easy to be caused can be calculated with high accuracy, and the minute defect can be detected with high accuracy.

Here, as the filter 205, as the filter for suppressing an occurrence of the elongating phenomenon, any of the space filters 401 through 404 indicated in any of FIG. 6A through FIG. 6B is adopted. By adopting such a space filter 205, the elongating phenomenon is suppressed in the image of the scattered light provided by taking the image by the imaging element 207. As a result, the separation of the defect coordinates calculated as the gravity center position of the illuminance distribution of the image of the scattered light provided by taking the image by the imaging element 207 and the defect coordinates on the actual sample is reduced, and the position of the defect can accurately be calculated from the detected image.

On the other hand, as the filter for the high sensitivity detection, the filter 411 or 412 configured by limiting the aperture to cut backward scattered light or a side scatter light component which is liable to be a noise component by passing the forward scattered light component as shown in, for example, FIG. 8A or FIG. 8B is used. The configuration of the space filter 411 shown in FIG. 8A is configured to pass the forward scattered light incident on the transmitting area 412 in scattered light generated from the sample 101 by the illumination light incident from a direction of the arrow 314, and shield scattered light incident on the portion of 413.

On the other hand, the space filter 421 shown in FIG. 8B is configured to pass forward scattered light incident on the portion 422 is scattered light generated from the sample 101 by the illumination light incident from the direction of the arrow 314, and completely shields scattered light incident on the portion of 425 since the light shielding rate of scattered light incident on the portion of 424 from the portion of 423 is gradually increased.

The scattered light passing through the filter for the high sensitivity detection as shown in FIG. 8A or FIG. 8B is focused by the focusing lens 206, a region having a luminance equal to or more than a threshold is extracted as a defect from the image of the scattered light provided by taking the image of the imaging element 207, and the gravity center position of the luminance value distribution of the image of the extracted defect is calculated as defect coordinates. The image of the detected defect and the position information of the defect are transmitted to be stored to the signal storing unit 223, and transmitted to the image display unit 222 to be displayed on the display screen 2221. Further, the image of the detected defect and the position information of the defect are transmitted to a processing device at a higher order via a communication network, not illustrated.

Although in the embodiment described above, an explanation has been given of a configuration of condensing a laser emitted from the light source 2011 by the illumination optical system unit 201 by the condensing lens 2012 to be irradiated onto the sample 101, the sample 101 may be illuminated by light formed in a linear shape by using a cylindrical lens for the condensing lens 2012. Further, although the explanation has been given of an example of carrying out inspection twice by switching the filter 205, there may be carried out a method of inspecting the front face of the sample 101 once by using a filter for suppressing the occurrence of the elongating phenomenon as the filter 205 without switching the filter 205.

According to the present embodiment, a defect image can be detected by reducing an occurrence of the elongating phenomenon in detecting a small defect on a sample by the dark visual field illumination, and a position of the defect can be detected with high accuracy.

Modified Example

An explanation will be given of a modified example of the defect detecting device 100 explained in the first embodiment in reference to FIG. 9.

The modified example differs in that two sets of illumination optical systems are provided to the optical microscope 1051 in the configuration of the defect detecting device 100 according to the first embodiment shown in FIG. 1. That is, the defect inspecting device 200 according to the modified example is configured by including an optical microscope 1051, the image processing unit 221, the image display unit 222, the signal storing unit 223, and a control unit 2241 as shown in FIG. 9. The control unit 2241 is connected to an exterior data processing unit by communicating means, not illustrated.

The optical microscope 1051 includes an illumination optical system unit 251 other than the illumination optical system unit 201 explained in the first embodiment. In FIG. 9, a configuration attached with a numeral the same as a numeral shown in FIG. 1 the same as the configuration explained in the first embodiment, and therefore, an explanation thereof will be omitted. Also the image processing unit 221, the image display unit 222, and the signal storing unit 223 stay the same as those explained in the first embodiment, and therefore, an explanation thereof will be omitted.

According to the modified example, the plural filters 2051 held by the filter holder 2081 include a filter that is suitable when the sample 101 is illuminated by the illumination optical system unit 201, and the filter that is suitable when the sample 101 is illuminated by the illumination optical system unit 251.

The illumination optical system unit 251 is configured by appropriately using a light source 2511, and a condensing lens 2512 for condensing to irradiate a light ray irradiated from the light source 2511 onto the sample 101 similarly to the illumination optical system unit 201. The illumination optical system unit 251 is arranged to the sample 101 in an azimuth angle direction the same as that of the illumination unit 101 and in a different elevation angle direction, and illuminates a region of the sample 101 the same as those of a region illuminated by the illumination unit 101.

The plural filters 2051 held by the filter holder 2081 also include filters following FIG. 6A and FIG. 6B or FIG. 7A and FIG. 7B in correspondence with the illumination optical system unit 251 other than filters in correspondence with the illumination optical system unit 201 as explained in reference to FIG. 6A and FIG. 6B or FIG. 7A and FIG. 7B in the first embodiment.

The control unit 2241 controls the illumination optical system unit 201 and the illumination optical system unit 251 by successively switching them for illuminating the sample 101 in inspection. That is, the control unit 2241 controls the driving the stage 103 to repeatedly scan the sample 101 in X direction or Y direction by. At the first scanning, carries out inspection by controlling the illumination optical system unit 201 to illuminate the sample 101 in a state of stopping illumination by the illumination optical system unit 251, and at the second time scanning, carries out inspection by controlling the illumination optical system unit 251 to illuminate the sample 101 in a state of stopping illumination by the illumination optical system unit 201.

The control unit 2241 carries out classification based on detection of a defect and an image characteristic amount of the defected defect by synthesizing a result of processing a signal detected by the imaging element 207 at the first time scanning by the image processing unit 221 and a result of processing a signal detected by the imaging element 207 at the second time scanning by the image processing unit 221 based on position information of a reference pattern (not illustrated) formed on the sample 101 provided by the result of detecting a signal detected by the imaging element 207 at the first scanning by the image processing unit 221, and position information of a reference pattern formed on the sample 101 provided by the result of detecting a signal detected by the imaging element 207 at the second scanning by the image processing unit 221.

In this way, the further detailed classification of the defect can be carried out by repeatedly carrying out an inspection in states of different illumination conditions and synthesizing to process the result.

Figure 9:
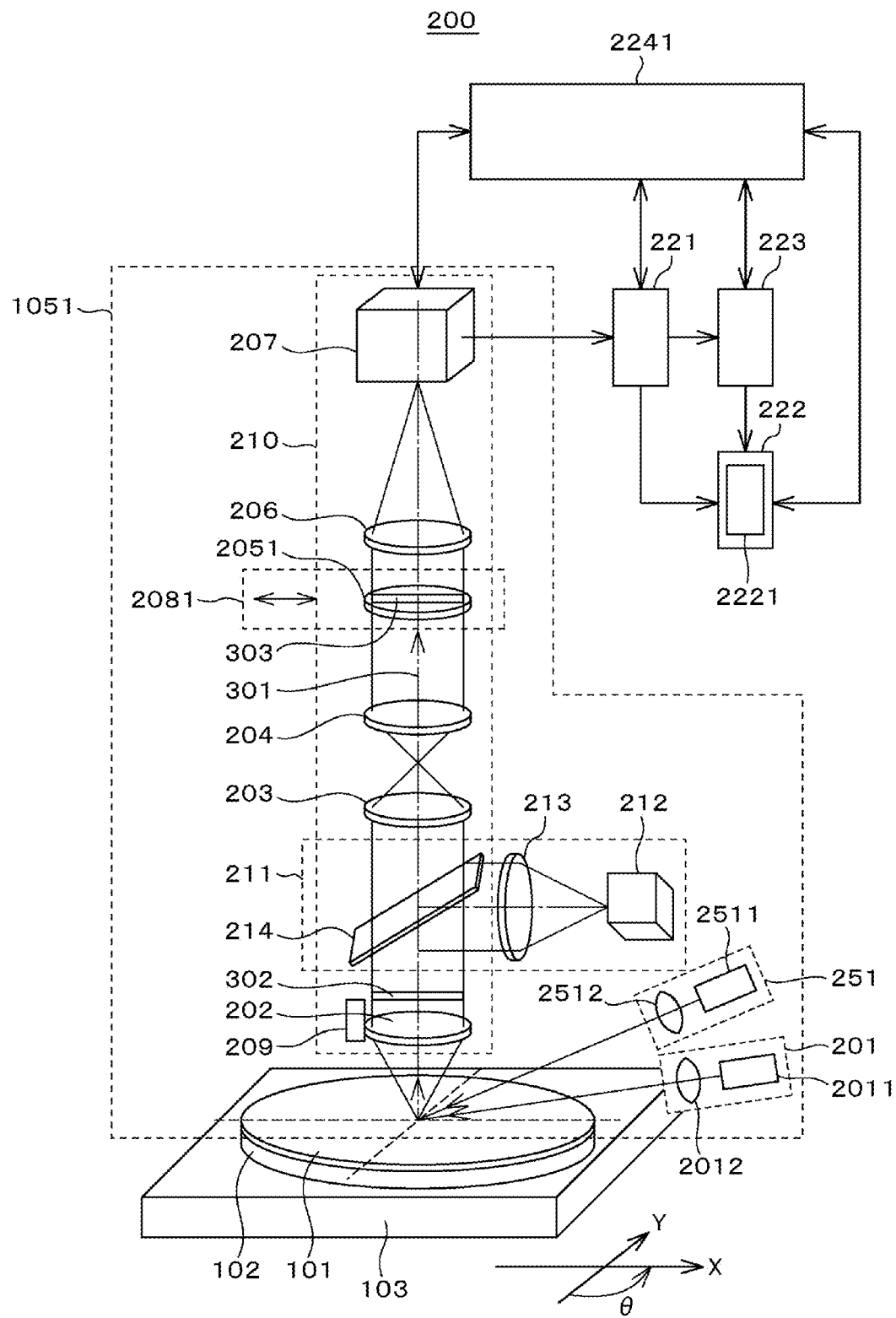
FIG. 9 is a block diagram showing an outline configuration of a defect detecting device according to a modified example of the first embodiment of the present invention.

Incidentally, although in the configuration shown in FIG. 9, the explanation has been given of the example of the two directions illumination having different elevation angles with the same azimuth angle, two-direction illumination may be carried out in which the elevation angle stay the same and the azimuth angle differs, and three-direction illumination combining these may be carried out. Also, there may be constructed a configuration of polarizing to illuminate the sample 101 by adding a polarization filter to the illumination optical system units 201 and 205.

Also, although in the configuration shown in FIG. 9, the illumination optical system unit 201 and the illumination optical system unit 251 respectively include the light sources 2011 or 2511, there may be constructed a configuration in which the light source is shared by the illumination optical system unit 201 and the illumination optical system unit 251 by using only one of the light source 2011 or 2511.

Second Embodiment

Next, as a second embodiment of the present invention, a detailed explanation will be given of an example of integrating the optical microscope 105 shown in FIG. 1 explained in the first embodiment to a review device in reference to the drawings.

Generally, in a case of observing a defect generated on a substrate in fabrication steps of a semiconductor device, the defect observation is carried out by the following defect observation procedure. First, an entire face of a sample is scanned by an inspection device, a defect present on the sample is detected, and coordinates where the defect is present are acquired. Next, a number of defects or a total of defects detected by the inspection device are observed in details by a review device based on the defect coordinates acquired by the inspection device and defect classification, a generated cause analysis, and the like are carried out.

Figure 10:
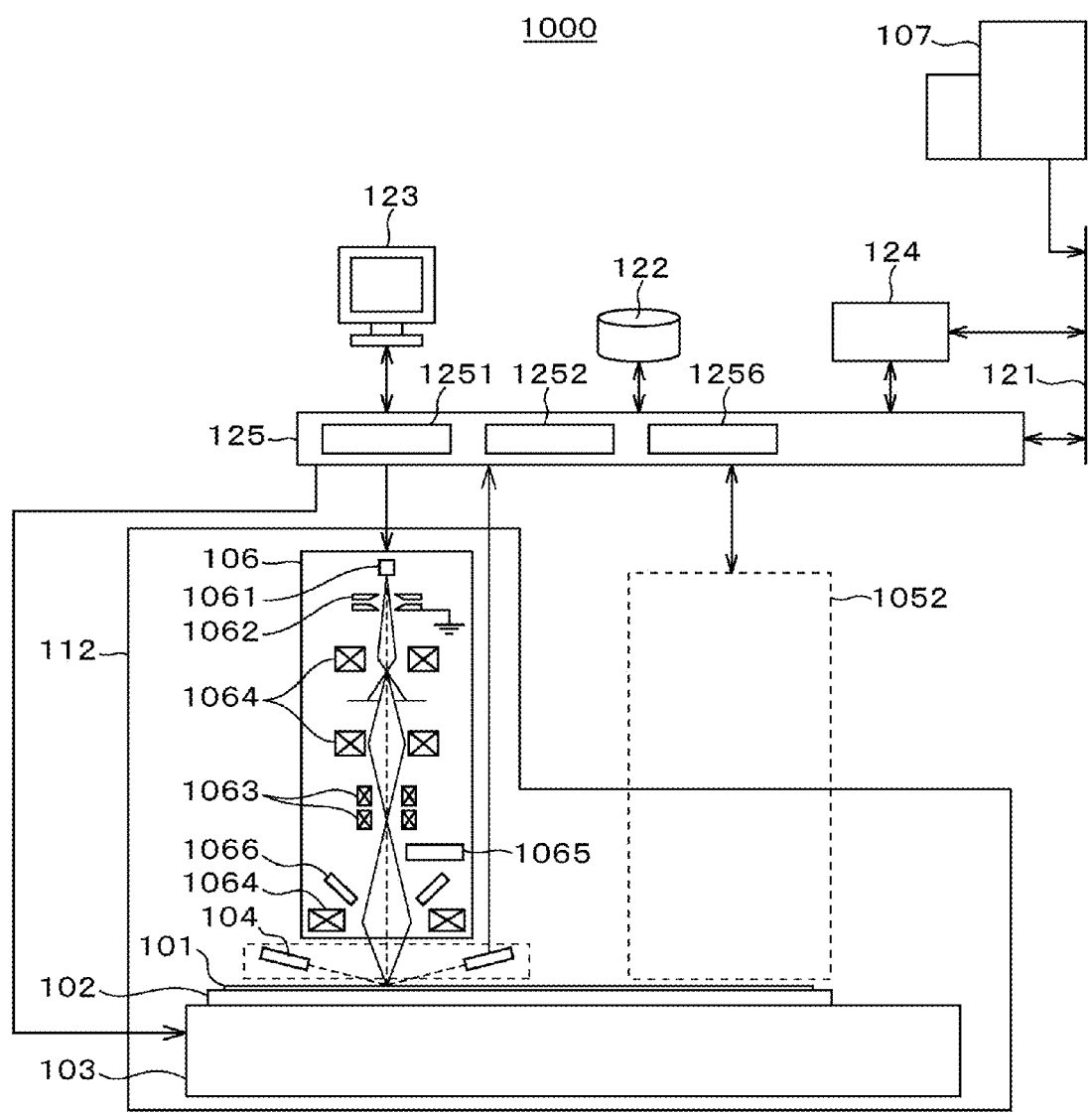
FIG. 10 is a block diagram showing an outline configuration of a review device according to a second embodiment of the present invention.

FIG. 10 shows an example of a configuration of a review device 1000 according to the present embodiment.

The review device 1000 of the present embodiment is configured by a sample holder 102 for mounting the sample 101 of the inspected object, a stage 103 capable of moving an entire face of the sample 101 below a scanning electron microscope 106 (hereinafter, described as SEM) by moving the sample holder 102, the SEM 106 for observing in details the sample 101, an optical height detecting system 104 for detecting a height of a surface of the sample 101 for aligning a focal point of the SEM 106 to the surface of the sample 101, an optical microscope 105 for optically detecting a defect of the sample 101 and acquiring detailed position information of the defect on the sample 101, a vacuum tank 112 for containing the SEM 106 and an objective lens of the optical microscope 105, a control system 125 of controlling the SEM 106, the optical height detecting system 104, and the optical microscope 105, a user interface 123, a library 122, a network 121 connected to a higher system of an inspection device 107 or the like, and a storing system 124 for preserving exterior data of the inspection device 107 or the like to provide to the control system.

The SEM 106 is configured by including an electron beam source 1061, an extraction electrode 1062 for extracting and accelerating a primary electron emitted from the electron beam source in a beam-like shape, a deflection electrode 1063 for controlling a trajectory of the primary electron beam extracted and accelerated by the extraction electrode, an objective lens electrode 1064 for converging the primary electron beam the trajectory of which is controlled by the deflection electrode to the surface of the sample 101, a secondary electron detector 1065 for detecting a secondary electron generated from the sample 101 irradiated with the primary electron beam the trajectory of which is controlled to converge, a reflection electron detector 1066 for detecting an electron having a comparatively high energy of a reflection electron or the like generated from the sample 101 irradiated with the converged primary electron beam at inside thereof.

The SEM 106 is arranged at an inner portion of the vacuum tank 112. Also a part of the optical microscope 1052 is further arranged at the inner portion of the vacuum tank 112.

Although the configuration and the function of the optical microscope 1052 is basically the same as those of the optical microscope 105 explained in reference to FIG. 1 through FIG. 7B in the first embodiment, what differs in the present embodiment is that a portion of the optical microscope 1052 is arranged at the inner portion of the vacuum tank 112 shared by the SEM 106.

Figure 11:
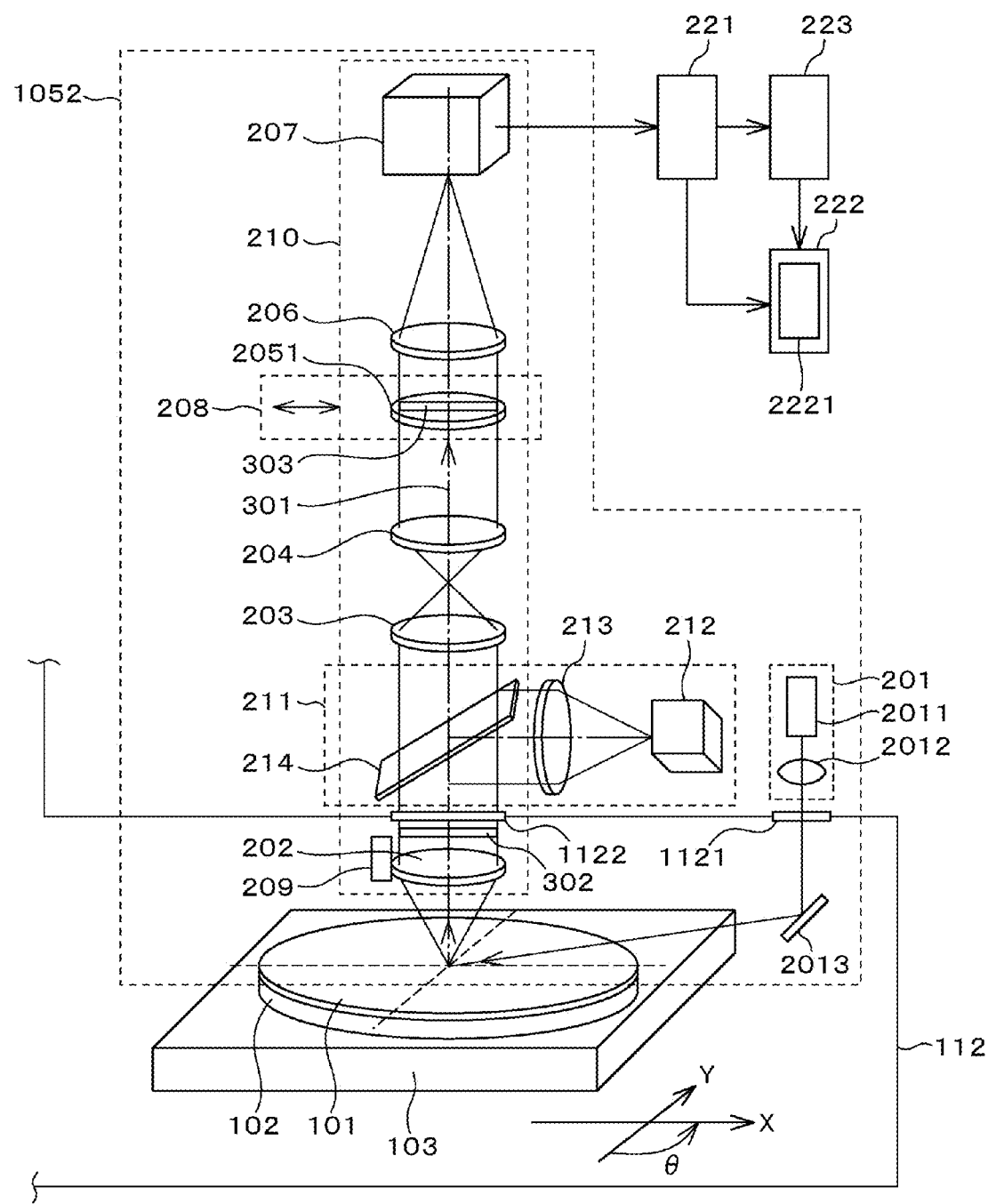
FIG. 11 is a block diagram showing an outline configuration of an optical microscope of a review device according to the second embodiment of the present invention.

That is, as shown in FIG. 11, the vacuum tank 112 is provided with a glass window 1121 for introducing illumination light emitted from the illumination unit. Also, the inner portion of the vacuum tank 112 is arranged with a mirror 2013 for converting an optical path of the introduced illumination light in a direction of the sample 101, and the objective lens 202 for condensing scattered light from the sample 101, and the height control mechanism 209 for adjusting a position in an optical axis direction of the objective lens 202 as portions of the optical microscope 1052, and a configuration of transmitting light condensed by the objective lens 202 through the glass window 1122 provided at the vacuum tank 112 to guide to the half mirror 214, the lenses 203 and 204, differs from a configuration of the optical microscope 105 according to the first embodiment explained in reference to FIG. 1.

The elongating phenomenon of the scattered light image and a configuration of the filter in correspondence therewith explained in reference to FIGS. 2 through 7B in the first embodiment are applied also to the present embodiment as they are.

The control system 125 includes an SEM control unit 1251 for controlling the SEM 106, an optical microscope control unit 1252 for controlling the optical microscope (corresponding to the control unit 224 according to the first embodiment shown in FIG. 1), and a total control unit 1256 for controlling a total of the review device 1000.

Further, the stage 103, the optical height detecting system 104, the optical microscope 105, the SEM 106, the user interface 123, the database 122, and the storing device 124 are connected to the control system 125, and the control system 125 is connected to higher order or upstream system (for example, the inspection device 107) via the network 121.

In the review device 1000 configured as described above, particularly, the optical microscope 1052 has a function of redetecting (hereinafter, described as detecting) a defect on the sample 101 detected by the inspection device 107 which is a higher order system by using position information of the defect detected by the inspection device 107, the optical height detection system 104 has a function of focusing means for focusing the primary electron beam for converging the primary electron beam of the SEM 106 to the surface of the sample 101, the control system 125 has a function of position correcting means for correcting position information of the defected detected by inspecting the defect by the other inspection device 107 based on the position information of the defect detected by the optical microscope 1052, and the SEM 106 is configured to have a function of observing the defect the position information of which is corrected by the control system 125. The stage 103 mounts the sample 101 and is moved between the optical microscope 1052 and the SEM 106 such that the defect detected by the optical microscope 1052 can be observed by the SEM 106.

Next, an explanation will be given of a general flow of processing in which the defect detected by the inspection device 107 (FIG. 10) is observed by the review device 1000 explained in reference to FIG. 10 by using FIG. 12.

First, the defect on the sample 101 is detected by using the inspection device 107 which is a higher or an upstream system, the other inspection device 107 outputs the inspection information of the sample 101 via the network 121, and inputs the inspection information to the storing device 124 of the review device 1000. The inspection information of the sample 101 outputted by the other inspection device 107 is the inspection information configured by an inspection result of defect coordinates, a defect signal, a defect shape, a polarization of defect scattered light, a defect kind, a defect label, a defect characteristic amount, and a scattered signal on the surface of the sample 101, or combinations of these, and an inspection condition configured by an illumination incidence angle, an illumination wavelength, an azimuth angle of illumination, an illumination intensity, and an illumination polarization of the other inspection device 107, an azimuth angle of the inspecting unit, an elevation angle of the inspecting unit, an inspection region of the inspecting unit or combinations of these. In a case where plural detectors are present in the other inspection device 107, inspection information provided as a result of inspecting the sample 101 outputted for the respective detectors or inspection information of the sample 101 synthesizing the plural detector outputs is used.

Next, some of defects extracted from the defects detected by the other inspection device 107 or all the defects are observed by the review device 1000 by using information stored to the storing device 124. First, a rough alignment of the sample 101 is carried out. This is carried out by bright visual field observation by the optical microscope 1052. Next, the stage 103 is moved so that a defect to be observed on the sample 101 falls within a visual field of the optical microscope 1052 by using the position information of the defect detected previously by the other inspection device 107 by the review device 1000 based on the defect coordinates acquired by the other inspection device 107 (Step 6001). Next, focusing is carried out by moving the objective lens 202 by the height control mechanism 209 (Step 6002).

Next, an image is acquired by the imaging element 207 of the optical microscope 1052 (Step 6003), the operation digitizes a luminance value of the acquired image (Step 6004), searches the defect within the image (Step 6005), if the defect is detected (Step 6006—YES), derives the defect coordinates from the luminance distribution of the defect image (Step 6007), if it is not necessary to detect other defects (Step 6008—NO), the defect detection by the optical microscope 1052 is finished (Step 6009). Further, a shift amount of a visual field position of the SEM 106 for the defect when the defect is going to be observed by the SEM 106 by using position information of the defect previously detected by the other inspection device 107 from a difference between coordinates of the defect detected by the optical microscope 1052 and position information of the defect previously detected by the other inspection device 107.

The position information of the defect detected previously by the other inspection device 107 is corrected based on the calculated shift amount, the defect the position information of which is corrected is moved to the visual field of the SEM 106 by driving the stage 103, and observation is carried out by the SEM 106. At this time, the observed information is transmitted to the control system 125, and registered to the database 122. Incidentally, in a case where there are a number of defects to be observed, representative several points thereamong are extracted, shift amounts of positions of defects previously detected by the other inspection device 107 and visual field positions of the SEM 106 are calculated from position information of the extracted defects previously detected by the other inspection device 107 and position information of the respective defects provided by detecting by the optical microscope 1052. By using the information of the calculated shift amounts, also concerning defects which are not detected by the optical microscope 1052 other than the representative several points, position information provided by previously detecting by the other inspection device 107 is corrected.

Next, in a case where other defect information is needed (Step 6008—YES), defect position information of a defect to be observed is acquired from an output result of the other inspection device 107, the operation returns to a procedure of moving the defect to the optical microscope 1052 (Step 6001), and advances the process according to the procedure. Incidentally, in a case where the defect cannot be detected by the defect detecting procedure described above (Step 6006—NO), it is conceivable that the defect is present at outside of the visual field of the optical microscope 1052, and therefore, a surrounding portion of the visual field of the optical microscope 1052 may be searched. In a case of searching the surrounding portion (Step 6010—YES), the sample 101 is moved by an amount in correspondence with the visual field (Step 6001), and the process is carried out from the defect detecting procedure described above. Also, in a case where the surrounding is not searched (step 6010—NO), the process is moved ahead in accordance with a procedure.

Next, in order to observe the defect detected by the other inspection device 107 (refer to FIG. 10) by the review device 1000 explained in reference to FIG. 10, an explanation will be given of a processing flow example in a case of detecting an observation object defect by the review device 1000 by using high sensitivity detection (hereinafter referred to as high sensitivity detection) by the dark visual field observation by the optical microscope 1052 having a possibility of bringing about the elongating phenomenon and means for suppressing the elongating phenomenon in reference to FIG. 13 through FIG. 15.

The other inspection device 107 is used to detect the defect on the sample 101, output inspection information of the sample 101 via the network 121 and input the inspection information to the storing device 124 of the review device 1000. The inspection information of the sample 101 outputted by the other inspection device 107 is inspection information configured by an inspection result configured any of defect coordinates, the defect signal, the defect shape, the polarization of defect scattered light, the defect kind, the defect label, the characteristic amount of the defect, and the scattering signal of a surface of the sample 101 or combinations of these, and the inspection condition configured by any of the illumination incidence angle, the illumination wavelength, the azimuth angle of the illumination, the illumination intensity, the illumination polarization of the other inspection device 107, the azimuth angle of detecting unit, the elevation angle of the detecting unit, and the detection region of the detecting unit or combinations of these. In a case where plural detectors are present at the other inspection device 107, inspection information provided as a result of inspecting the sample 101 outputted for each detector or inspection information of the sample 101 synthesizing the plural detector outputs is used.

Figure 13:
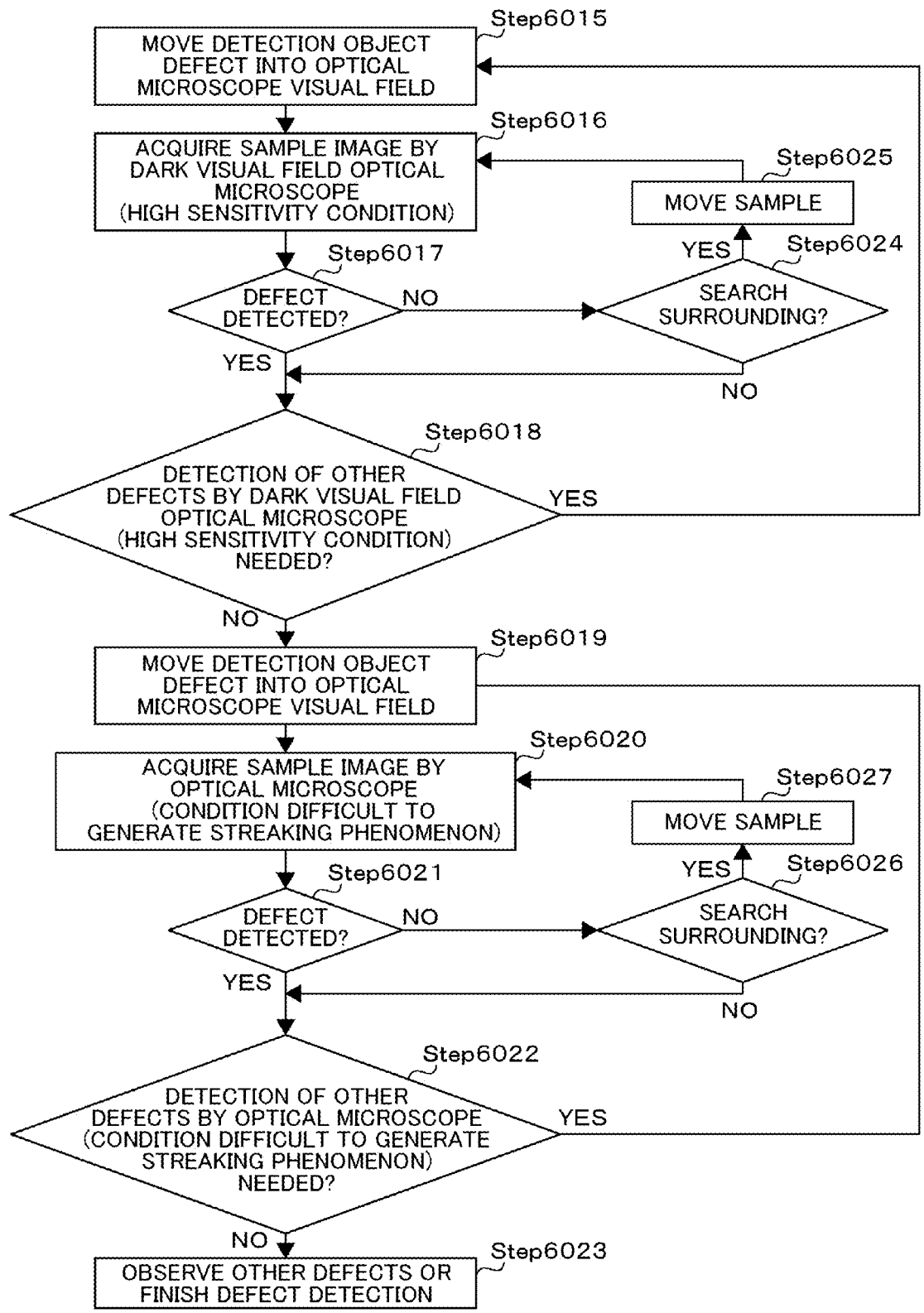
FIG. 13 is a flowchart of explaining an example of a procedure of detecting a defect by an optical inspection device according to the second embodiment of the present invention.

FIG. 13 shows a processing flow example in a case of taking an image and inspecting all of detection object defects under plural optical conditions of high sensitivity detecting condition and the elongating phenomenon suppressing condition. First, the stage 103 is moved such that a defect intended to be observed on the sample 101 falls within the visual field of the dark visual field of the optical microscope 1052 set to the high sensitivity condition by using the position information of the defect previously by the other inspection device 107 by the review device 1000 based on the defect coordinates acquired by the other inspection device 107 (Step 6001). Next, focusing is carried out by moving the objective lens 202 by the height control mechanism 209, an image acquired by the imaging element 207 of the dark visual field observation by the optical microscope 1052 set to the high sensitivity condition is acquired (Step 6016), the defect is searched within the acquired image, if the defect is detected (Step 6017—YES), the defect coordinates are derived from the luminance distribution of the defect image.

Next, in a case where the other defect information is needed by the dark visual field observation by the optical microscope 1052 set to the high sensitivity condition (Step 6018—YES), defect position information to be observed is acquired from an output result of the other inspection device 107, the operation returns to a procedure of moving the defect to the dark visual field of the optical microscope 1052 set to the high sensitivity condition described above (Step 6015), and the operation advances the process according to the procedure. Incidentally, in a case where the defect cannot be detected by the defect detecting procedure described above (Step 6017—NO), it is conceivable that the defect is present at outside of the visual field of the dark visual field of the optical microscope 1052 set to the high sensitivity condition, and therefore, a surrounding of the visual field of the dark visual field of the optical microscope 1052 set to the high sensitivity condition to be searched.

In a case of searching the surrounding portion (Step 6024—YES), the sample 101 is moved by an amount in correspondence with the visual field (Step 6025), and the operation advances the process according to the procedure from the defect detecting procedure described above. Also, in a case where the surrounding is not need to be searched (Step 6024—NO), the operation advances the process according to the procedure. Next, when it is not necessary to detect other defects by the dark visual field observation by the optical microscope 1052 set to the high sensitivity condition (Step 6018—NO), the stage 103 is moved by using the position information of the defect detected by the other inspection device 107 so that the defect falls into the visual field of the dark visual field of the optical microscope 1052 set to the optical condition of suppressing the elongating phenomenon (Step 6019).

Next, the focusing is carried out by moving the objective lens 202 by the height control mechanism 209, an image is taken by taking the image by the imaging element 207 in a state in which the dark visual field observation by the optical microscope 1502 is set to an optical condition suppressing the elongating phenomenon (Step 6020), a defect is searched in the taken image, if a defect is detected (Step 6021—YES), and defect coordinates are derived from a luminance distribution of a defect image. If it is not necessary to detect other defects (Step 6022—NO), the defect detection by the dark visual field observation by the optical microscope 1052 is finished (Step 6023).

Next, in a case where other defect information is needed in a state of setting the dark visual field observation by the optical microscope 1052 to an optical condition suppressing the elongating phenomenon (Step 6022—YES), defect position information of a defect to be observe is acquired from an output result of the other inspection device 107, the operation returns to a procedure of moving the defect to the dark visual field of the optical microscope 1502 described above (Step 6019), and moves the process ahead.

Incidentally, in a case where the defect cannot be detected by the defect detecting procedure described above (Step 6021—NO), it is conceivable that the defect is present at outside of the visual field of the dark visual field of the optical microscope 1052, and therefore, a surrounding portion of the visual field of the dark visual field of the optical microscope 1052 may be searched. In a case where the surrounding portion is searched (Step 6026—YES), the sample 101 is moved by an amount in correspondence with the visual field (Step 6027), and the operation advances the process according to the procedure by the defect detecting procedure described above. Also, in a case where the surrounding is not searched (Step 6026—NO), the operation advances the process according to the procedure in accordance with the procedure.

Further, the shift amount of the visual field position of the SEM 106 for the defect when the defect is going to be observed by the SEM 106 is calculated by using position information of the defect detected previously by the other inspection device 107 from the difference between the defect coordinates provided in a state in which the dark visual field observation by the optical microscope 1052 is set to the high sensitivity condition or the optical condition suppressing the elongating phenomenon and the position information of the defect previously detected by the other inspection device 107. The position information of the defect detected previously by the other inspection device 107 is corrected based on the calculated shift amount, and the defect which is corrected the position information is moved to the visual field of the SEM 106 to carry out observation. At this time, the observed information is transmitted to the control system 125, and registered to the database 122.

Incidentally, in a case where there are a number of defects to be observed, representative several points thereamong are extracted, and the shift amount of the position of the defect previously detected by the other inspection device 107 and the visual field position of the SEM 106 is calculated from the detected position information of the extracted defects detected previously by the other inspection device 107 and position information of the respective defects provided by the detection with the optical microscope. Also concerning the defects which are not detected by the optical microscope other than the representative several points, the position information provided by previously detecting by the other inspection device 107 is corrected by using the information of the calculated shift amount.

It is all right to use either of defect coordinates derived from an acquired image of the dark visual field observation by the optical microscope 1052 set to the high sensitivity condition (hereinafter, referred to as high sensitivity means deriving defect coordinates) or defect coordinates derived from an acquired image of the dark visual field observation by the optical microscope 1052 set to the optical condition suppressing the elongating phenomenon (hereinafter, referred to as suppressing means deriving defect coordinates).

When separation between the high sensitivity means deriving defect coordinates and the elongating suppressing means deriving defects coordinates is equal to or larger than a threshold, the elongating suppressing means deriving defect coordinates are used; and when the separation is less than the threshold, there is a method of using the high sensitivity means deriving defect coordinates, or a method of determining presence or absence of generating the elongating phenomenon from a direction of separating the high sensitivity means deriving defect coordinates and the elongating suppressing means deriving defect coordinates, using the elongating phenomenon suppressing means deriving defect coordinates when it is known that the elongating phenomenon is generated, and using the high sensitivity means deriving defect coordinates when the elongating phenomenon is not generated. Further, a defect which is detected only from an image taken by either one of the dark visual field optical microscope of the high sensitivity condition or the optical microscope of the optical condition suppressing the elongating phenomenon is provided with defect coordinates by using a taken image of the detected condition.

According to the method shown in FIG. 13, in a case where a number of detection object defects is large, detection time is taken, and there is a concern of reducing a throughput. Hence, next, an explanation will be given of a processing flow in a case where first, the elongating phenomenon suppressing means is used, images of all of object defects are taken and inspected, then, images are taken and inspected by using the high sensitivity detecting means with an object of a defect which cannot be detected by the elongating phenomenon suppressing means in reference to FIG. 14.

First, the stage 103 is moved so that a defect to be observed on the sample 101 falls within the visual field of the dark visual field of the optical microscope 1052 set to the optical condition suppressing the elongating phenomenon by using position information of the defect detected previously by the other inspection device 107 by the review device 1000 based on the defect coordinates acquired by the other inspection device 107 (Step 6028). Next, focusing is carried out by moving the objective lens 202 by the height control mechanism 209, an image taken by the dark visual field observation by the optical microscope 1052 set to the optical condition of suppressing the elongating phenomenon is acquired (Step 6029), a defect is searched within the acquired image, when the defect is detected (Step 6030—YES), and the defect coordinates are derived from the luminance distribution of the defect image.

When it is not necessary to detect other defects by the dark visual field observation by the optical microscope 1052 set to the optical condition of suppressing the elongating phenomenon (Step 6031—NO), since a defect is detected by the dark visual field observation by the optical microscope 1052 set to the optical condition suppressing the elongating phenomenon (Step 6032—YES), it is not necessary to detect a defect by the dark visual field observation by the optical microscope 1052 set to the high sensitivity condition (Step 6036—NO), and the defect detection is finished (Step 6037).

Next, in a case where other defect information is needed by the dark visual field observation by the optical microscope 1052 set to the optical condition of suppressing the elongating phenomenon (Step 6031—YES), the defect position information to be observed is acquired from an output result of the other inspection device 107, the operation returns to a procedure of moving a defect to the dark visual field of the optical microscope 1052 set to the optical condition of suppressing the elongating phenomenon described above (Step 6028), and advances the process according to the procedure. Incidentally, in a case where the defect cannot be detected by the defect detecting procedure described above (Step 6030—NO), it is conceivable that the defect is present at outside of the visual field of the dark visual field of the optical microscope 1052 set to the optical condition suppressing the elongating phenomenon, and therefore, a surrounding portion of the visual field of the dark visual field of the optical microscope 1052 may be searched.

In a case of searching the surrounding portion (Step 6038—YES), the sample 101 is moved by an amount in correspondence with the visual field (Step 6039), and the operation advances the process according to the procedure from the defect detecting procedure described above. Further, in a case where the surrounding is not need to be searched (Step 6038—NO), the operation advances the process according to the procedure.

Further, in a case where the defect cannot be detected by the dark visual field observation by the optical microscope 1052 set to the optical condition of suppressing the elongating phenomenon (Step 6030—YES), a defect cannot be detected even when a surrounding is searched and an image is taken, and the search for surrounding is finished (Step 6038—NO), the defect cannot be detected by the dark visual field observation by the optical microscope 1052 set to the optical condition of suppressing the elongating phenomenon (Step 6032—NO). In this case, the defect is detected by the dark visual field observation by the optical microscope 1052 set to the high sensitivity condition, and therefore, the stage 103 is moved so that the defect to be observed on the sample 101 falls within the visual field of the dark visual field of the optical microscope 1052 set to the high sensitivity condition by using the position information of the defect previously detected by the other inspection device 107 (Step 6033).

Next, an image is acquired by taking the image by the dark visual field observation by the optical microscope 1052 set to the high sensitivity condition (Step 6034), the defect is searched within the acquired image, when the defect is detected (Step 6035—YES), the defect coordinates are derived from the luminance distribution of the defect image. Next, in a case where other defect information is needed by the dark visual field observation by the optical microscope 1052 set to the high sensitivity condition (Step 6036—YES), defect position information to be observed is acquired from an output result of the other inspection device 107, the operation returns to a procedure of moving the defect to the dark visual field of the optical microscope described above (Step 6032), and advances the process according to the procedure.

Incidentally, in a case where the defect cannot be detected by the defect detecting procedure described above (Step 6035—NO), it is conceivable that the defect is present at outside of the visual field of the dark visual field of the optical microscope 1052, and therefore, a surrounding portion of the visual field of the dark visual field of the optical microscope 1052 may be searched. In a case of searching the surrounding portion (Step 6040—YES), the sample 101 is moved by an amount in correspondence with the visual field (Step 6041), and the operation advances the process according to the procedure from the defect detecting procedure described above. Further, in a case where the surrounding is not need to be searched (Step 6040—NO), the operation advances the process according to the procedure. Further, a shift amount of a visual field position of the SEM 106 relative to a defect position information of the defect previously detected by the other inspection device 107 is calculated from a difference between the defect coordinates provided by using the dark visual field observation by the optical microscope 1052 set to the optical condition of suppressing the elongating phenomenon or the dark visual field observation by the optical microscope 1052 set to the high sensitivity condition and position information of the defect previously detected by the other inspection device 107.

Position information of the defect previously detected by the other inspection device 107 is corrected based on the calculated shift amount, and the defect the position information of which is corrected is moved to the visual field of the SEM 106 and is observed. At this time, the observed information is transmitted to the control system 125 and is registered to the database 122.

Incidentally, in a case where there are a number of defects to be observed, presentative several points thereamong are extracted, and a shift amount of a position of the defect previously detected by the other inspection device 107 and a visual field position of the SEM 106 is calculated from position information of the extracted defects previously detected by the other inspection device 107 and position information of respective defects provided by detecting the dark visual field observation by the optical microscope 1052 set to the optical condition of suppressing the elongating phenomenon or the dark visual field observation by the optical microscope 1052 set to the high sensitivity condition. By using the information of the calculated shift amount, the position information provided by previously detecting by the other inspection device 107 is corrected also with respect to defects other than the representative several points which are not detected by the dark visual field observation by the optical microscope 1052 set to the optical condition of suppressing the elongating phenomenon or the dark visual field observation by the optical microscope 1052 set to the high sensitivity condition.

Next, an explanation will be given of a processing flow in a case where output information of the other inspection device 107 is used, inspecting means is selected for respective detection object defects, and an image is taken and inspected by using the selected inspecting means for shortening a throughput in reference to FIG. 15.

First, an optical microscope detecting condition of the detection object defect is determined from an inspection result outputted by the other inspection device 107 (Step 6043). As information used for the determination, defect coordinates, wafer information, a luminance of a defect, a defect size, class information of a defect, or characteristic amounts based thereon are used. For example, in a case of using the luminance value of defect scattered light, a defect having the luminance equal to or larger than a threshold is detected by setting the dark visual field observation by the optical microscope 1052 to the optical condition of suppressing the elongating phenomenon, and a defect of the luminance equal to or smaller than the threshold is detected by setting the optical condition of the dark visual field observation by the optical microscope 1052 to the high sensitivity condition. Otherwise, there is a method in which in a case where plural detection sensors are present in the other detection device 107, a defect having a large sensor output of a front/low angle region is detected by setting the dark visual field observation by the optical microscope 1052 to an optical condition of suppressing the elongating phenomenon, and other defects are detected by setting the optical condition of the dark visual field observation by the optical microscope 1052 to the high sensitivity condition.

Next, the defect is detected by the detection method determined at Step 6043. Concerning the defect detected in a state in which an optical condition of the dark visual field observation by the optical microscope 1052 is set to an optical condition of suppressing the elongating phenomenon (Step 6044—YES), the stage 103 is moved so that the defect to be observed on the sample 101 falls within the visual field of the optical microscope by using position information of the defect previously detected by the other inspection device 107 by the review device 1000 based on defect coordinates acquired by the other inspection device 107 (Step 6045). Next, focusing is carried out by moving the objective lens 202 by the height control mechanism 209, the image taken by the imaging element 207 of the dark visual field observation by the optical microscope 1052 is acquired (Step 6046), the defect is searched within the acquired image, and when the defect is detected (Step 6047—YES), defect coordinates are derived from the luminance distribution of the defect image.

Next, in a case where other defect information is needed by the dark visual field observation by the optical microscope 1052 set to an optical condition of suppressing the elongating phenomenon (Step 6048—YES), defect position information to be observed is acquired from an output result of the other inspection device 107, the operation returns to a procedure of determining the optical microscope inspection condition of the defect described above (Step 6044), and advances the process according to the procedure. Incidentally, in a case where the defect cannot be detected by the defect inspecting procedure described above (Step 6047—NO), it is conceivable that the defect is present at outside of the visual field of the dark visual field of the optical microscope 1052, and therefore, a surrounding portion of the visual field of the dark visual field of the optical microscope 1052 may be searched. In a case of searching the surrounding portion (Step 6055—YES), the sample 101 is moved by an amount in correspondence with the visual field (Step 6056), and the operation advances the process according to the procedure from the defect detecting procedure described above. Further, in a case where the surrounding is not need to be searched (Step 6055—NO), the operation advances the process according to the procedure.

When it is not necessary to detect other defects by the dark visual field observation by the optical microscope 1052 set to an optical condition of suppressing the elongating phenomenon (Step 6048—NO), in a case where the detecting means determined at Step 6043 detects the defect by the dark visual field observation by the optical microscope 1052 set to the high sensitivity condition (Step 6049—YES), the stage 103 is moved by using position information of the defect detected by the other inspection device 107 so that the defect falls within the visual field of the dark visual field of the optical microscope 1052 set to the high sensitivity condition (Step 6050).

Next, focusing is carried out by moving the objective lens 202 by the height control mechanism 209, the image is acquired by taking the image by the imaging element 207 of the dark visual field observation by the optical microscope 1052 set to the high sensitivity condition (Step 6051), the defect is searched within the acquired image, and when the defect is detected (Step 6052—YES), defect coordinates are derived from the luminance distribution of the defect image. When it is not necessary to detect other defects (Step 6053—NO), the defect detection by the dark visual field observation by the optical microscope 1052 is finished (Step 6054).

Next, in a case where other defect information is needed by the dark visual field observation by the optical microscope 1052 set to the high sensitivity condition (Step 6053—YES), defect position information of a defect to be observe is acquired from an output result of the other inspection device 107, the operation returns to a procedure of moving the defect to the dark visual field optical microscope 105 described above (Step 6050), and advances the process according to the procedure.

Incidentally, in a case where the defect cannot be detected by the defect detecting procedure described above (Step 6052—NO), it is conceivable that the defect is present at outside of the visual field of the optical microscope 1052, and therefore, the surrounding portion of the visual field of the optical microscope 1052 may be searched. In a case of searching the surrounding portion (Step 6058—YES), the sample 101 is moved by an amount in correspondence with the visual field (Step 6059), and the operation moves the processing ahead from the defect detecting procedure described above. Further, in a case where the surrounding is not need to be searched (Step 6058—NO), the operation advances the process according to the procedure.

Further, a shift amount of the visual field position of the SEM 106 relative to the defect is calculated when the defect is going to be observed by the SEM 106 by using position information of the defect previously detected by the other inspection device 107 from a difference between the defect coordinates provided by using the dark visual field observation by the optical microscope 1052 set to the optical condition of suppressing the elongating phenomenon or the dark visual field observation by the optical microscope 1052 set to the high sensitivity condition and position information of the defect previously detected by the other inspection device 107. Position information of the defect detected previously by the other inspection device 107 is corrected based on the calculated shift amount, the defect the position information of which is corrected is moved to the visual field of the SEM 106 to carry out observation.

At this time, observed information is transmitted to the control system 125, and is registered to the database 122. Incidentally, in a case where there are a number of defects to be observed, representative several points thereamong are extracted, and a shift amount of a position of the defect previously detected by the other inspection device 107 and a position of a visual field of the SEM 106 is calculated from position information previously detected by the other inspection device 107 of the extracted defects and position information of respective defects provided by detecting by the optical microscope of the optical condition of suppressing the elongating phenomenon or the dark visual field optical microscope of the high sensitivity condition.

By using the information of the calculated shift amount, the position information provided by previously detecting the other inspection device 107 is corrected also concerning by the defect which are not detected by the dark visual field observation by the optical microscope 1052 other than the representative several points. Further, regarding the optical microscope inspection condition determined at Step 6043, in the defect of the detection object by the dark visual field observation by the optical microscope 1052 set to the high sensitivity condition, the defect which cannot be detected by the dark visual field observation by the optical microscope 1052 set to the high sensitivity condition (Step 6052—NO) may be detected by setting the dark visual field observation by the optical microscope 1052 to the optical condition of suppressing the elongating phenomenon (not illustrated).

In the dark visual field observation by the optical microscope 1052, as a method of switching the high sensitivity detection condition and detection of an optical condition of suppressing the elongating phenomenon, the filter holder 208 (FIG. 11) is moved, and the filter 205 on the optical axis is changed. When the filter 205 is switched, not a slide type as in the filter holder 208 but a filter holder of a rotating revolver type may be used. For suppressing the elongating phenomenon, as the filter 205 (FIG. 11), one or plural filter(s) or polarizer(s) described in FIG. 6A or 6B or FIG. 7A or 7B in the first embodiment may be used. Further, in a case of using MEMS or a liquid crystal for the filter 205, there is a method of not switching by the filter holder 208 but switching by changing an optical property by an applied voltage.

Figure 14:
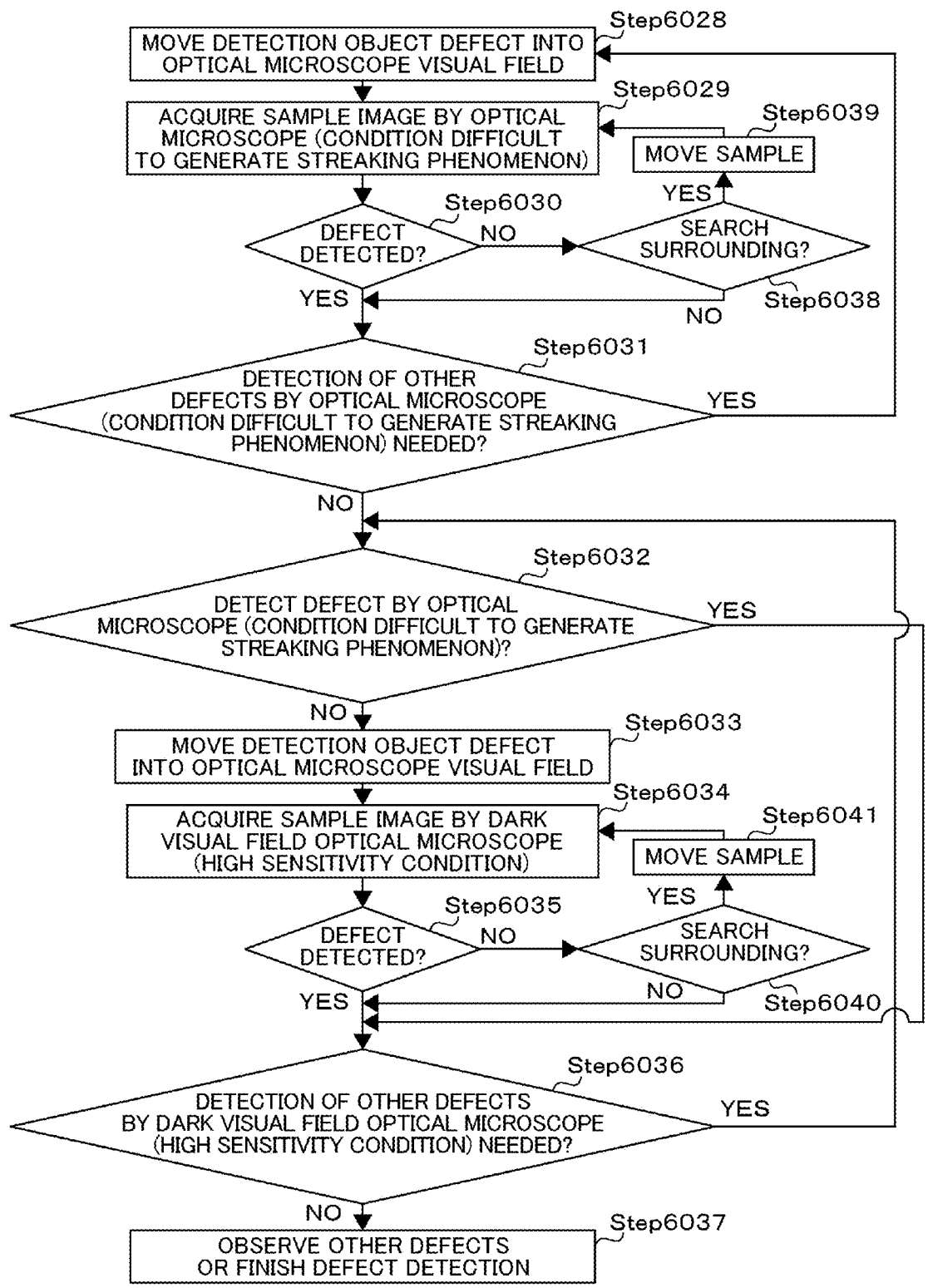
FIG. 14 is a flowchart of explaining an example of a procedure of detecting a defect by an optical inspection device according to the second embodiment of the present invention.

Further, in a case of using the filter 403 or 404 or the polarizer partially operating to the front low angle region as shown in FIG. 7A or 7B, the elongating phenomenon is suppressed, and a reduction in a sensitivity is small, and therefore, the high sensitivity means and the elongating phenomenon suppressing means of a processing flow explained in reference to FIG. 13 through FIG. 15 may or may not properly be used.

Next, a description will be given of a method of maintaining defect coordinates alignment accuracy by determining whether the elongating phenomenon is generated or not generated, and selecting the defect coordinate deriving algorithm in accordance with the result. Thereby, although the defect cannot be detected in a case where an optical condition for suppressing the elongating phenomenon is difficult to be mounted as well as in the dark visual field observation by the optical microscope 1052 setting the optical condition for suppressing the elongating phenomenon, in the dark visual field observation by the optical microscope 1052 setting the high sensitivity condition, the defect coordinates alignment accuracy can highly be maintained even in the elongating defect.

As a method of determining whether the elongating phenomenon is generated in the dark visual field acquired at the dark visual field observation by the optical microscope 1052 (FIG. 11), there is a method of determining the elongating phenomenon from a shape of a defect dark visual field image acquired by the dark visual field observation by the optical microscope 1052, or a method of determining the elongating phenomenon by comparing plural sheets of dark visual field images acquired by different optical conditions by using the dark visual field observation by the optical microscope 1052. Hereinafter, in the defect dark visual field image acquired by the dark visual field observation by the optical microscope 1052, a defect in which the elongating phenomenon is generated is referred to as elongating defect, and a defect in which the elongating phenomenon is not generated is referred to as non-elongating defect.

As a method of determining whether a elongating defect is brought about from a defect dark visual field image acquired by the dark visual field observation by the optical microscope 1052, there is a method of using a characteristic amount provided from a shape of the defect dark visual field image. For example, there are characteristic amounts based on an angle of inclination of the defect dark visual field image, a size of the defect dark visual field image occupied in the visual field of the dark visual field observation by the optical microscope 1052, or a ratio to the region, a ratio of a long axis to a short axis of the defect dark visual field image, or combinations of these. A defect in which the characteristic amount provided from a shape of the defect dark visual field image satisfies a set value is determined as a elongating defect, and the other is determined as a non-elongating defect. An advantage of the method resides in that a time period necessary for detecting the defect is short since it is not necessary to acquire the dark visual field image of the defect defect under plural conditions.

In a method of determining whether a elongating defect is brought about by comparing plural dark visual field images acquired by the different optical conditions by using the dark visual field observation by the optical microscope 1052, as the different optical conditions, there are, for example, illumination intensity, an accumulating time of the imaging element 207, an incidence azimuth angle of illumination to a defect or the like. As a method of changing the incidence azimuth angle of illumination, there is a method of rotating a wafer, or a method of switching incidence azimuth angle of a laser emitted from the illumination optical system unit 201 to a wafer. For example, in a case of switching the incidence azimuth angle of the laser by $\pi/2$, in the elongating defect of elongating a long tail from the incidence azimuth, the elongating direction is changed by $\pi/2$ by the incidence azimuth angle of the laser. Further, in a case of reducing the illumination intensity or in a case of shortening the image acquisition accumulating time of the imaging element 207, in the elongating defect, a change of the shape of the defect dark visual field image is anisotropic (tail is shortened). However, in a non-elongating defect, the shape of the defect dark visual field image is changed substantially isotropically.

Figure 16:
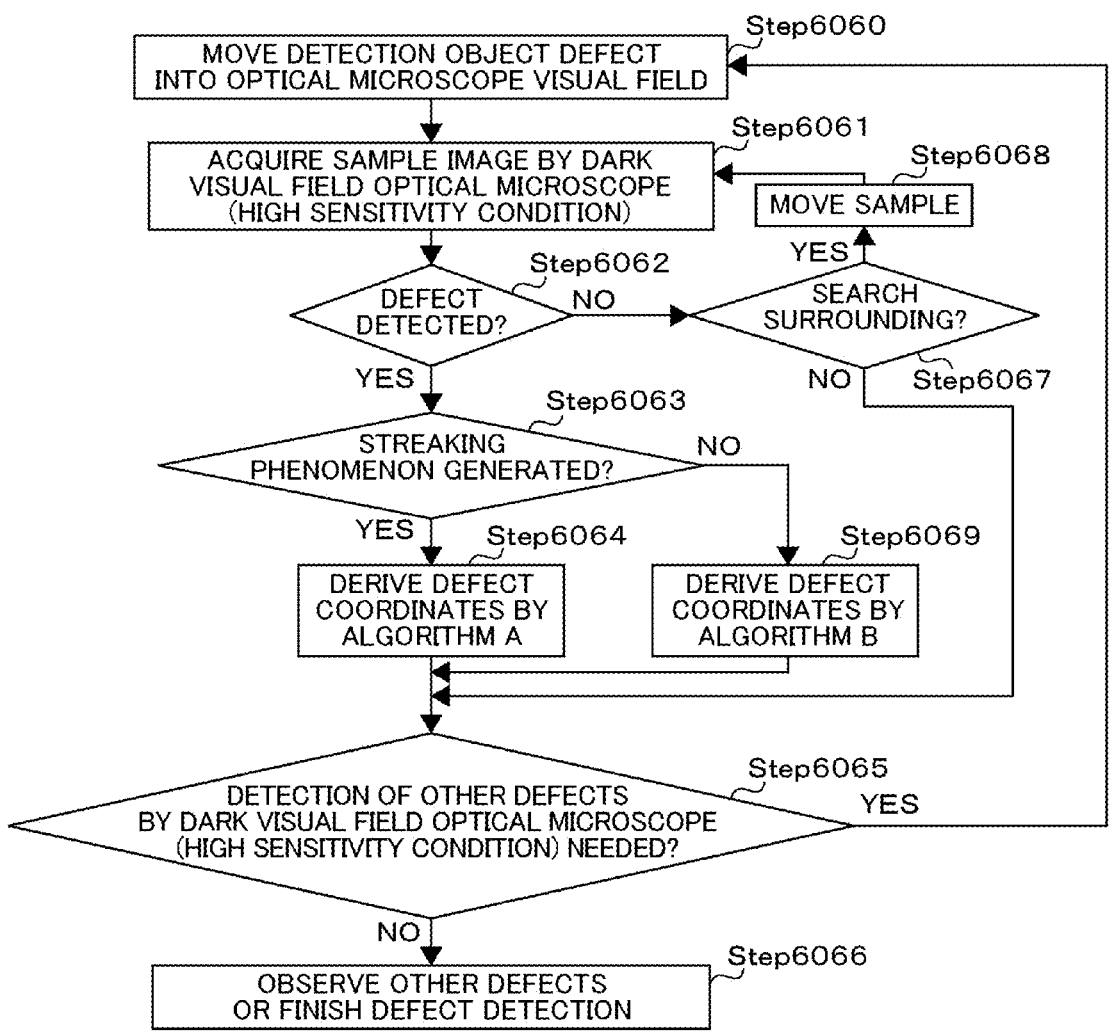
FIG. 16 is a flowchart of explaining an example of a procedure of detecting a defect by an optical inspection device according to the second embodiment of the present invention.

Next, an explanation will be given of a defect coordinate detection processing flow in a case of determining whether a detected defect is a elongating defect or a non-elongating defect and selecting a defect coordinate detection algorithm based on a result of the determination, by referring to FIG. 16.

First, the stage 103 of the review device 1000 is moved so that a defect to be observed on the sample 101 falls within the visual field of the dark visual field observation by the optical microscope 1052 by using position information of the defect previously detected by the other inspection device 107 (Step 6060). Next, focusing is carried out by moving the objective lens 202 by the height control mechanism 209, an image is taken by the dark visual field observation by the optical microscope 1052 (Step 6061), the defect is searched within the acquired image, and if the defect is detected (Step 6017—YES), then, it is determined whether a elongating defect or not from the image acquired at Step 6061.

When the object defect is the elongating defect (Step 6063—YES), the defect coordinates are derived from the luminance distribution of the defect image by using algorithm A for the elongating defect (Step 6064). Also, when the object defect is a non-elongating defect (Step 6063—NO), defect coordinates are derived from the luminance distribution of the defect image by using algorithm B for the non-elongating defect. For example, as algorithm A, there is a method of digitizing the acquired image by the luminance value, and making an end in a direction inverse to a tail (left end in a case of the dark visual field image 384 of FIG. 2(b)) defect coordinates. And for example, as algorithm B, there is a method of digitizing an acquired image by the luminance value and making luminance gravity center defect coordinates.

As a method of determining whether the detected defect is a elongating defect or a non-elongating defect, there is a method of using a characteristic amount provided from a shape of a defect dark visual field image acquired by the dark visual field observation by the optical microscope 1052. For example, there are characteristic amounts based on an angle of inclination of a defect dark visual field image, a size of the defect dark visual field image occupied in a visual field of the dark visual field observation by the optical microscope 1052, or a ratio to a region, a ratio of a long axis to a short axis of the defect dark visual field image, or combinations of these. A defect in which the characteristic amount provided from the shape of the defect dark visual field image satisfies a set value is determined to be the elongating defect, and others are determined to be the non-elongating defect. For example, in a case of a defect in a convex shape of a low stepped difference strongly scatters in a front low elevation angle direction, a tail is streaked in a direction in parallel with an incidence face of illumination light, and therefore, in a case where an angle of inclination of the defect dark visual field image is near to an incidence azimuth angle of illumination light, it is conceivable to determine the defect as a elongating defect.

Next, in a case of needing other defect information by the dark visual field observation by the optical microscope 1052 (Step 6065—YES), defect position information to be observed is acquired from an output result of the other inspection device 107, the operation returns to a procedure of moving the defect to the dark visual field of the optical microscope 1052 set to the high sensitivity condition described above (Step 6060), and proceeding the process ahead.

Further, in a case where a defect cannot be detected by the defect detecting procedure described above (Step 6062—NO), it is conceivable that the defect is present at outside of the visual field of the dark visual field of the optical microscope 1052, and therefore, a surrounding portion of the visual field of the dark visual field of the optical microscope 1052 may be searched. In a case of searching the surrounding portion (Step 6067—YES), the sample 101 is moved by an amount in correspondence with the visual field (Step 6068), and the operation advances the process according to the procedure from the defect detecting procedure described above. Further, when the surrounding is not need to be searched (Step 6067—NO), the operation advances the process according to the procedure. Next, when it is not necessary to detect other defects by the dark visual field observation by the optical microscope 1052 (Step 6065—NO), the defect detection by the optical microscope is finished (Step 6066).

Figure 17:
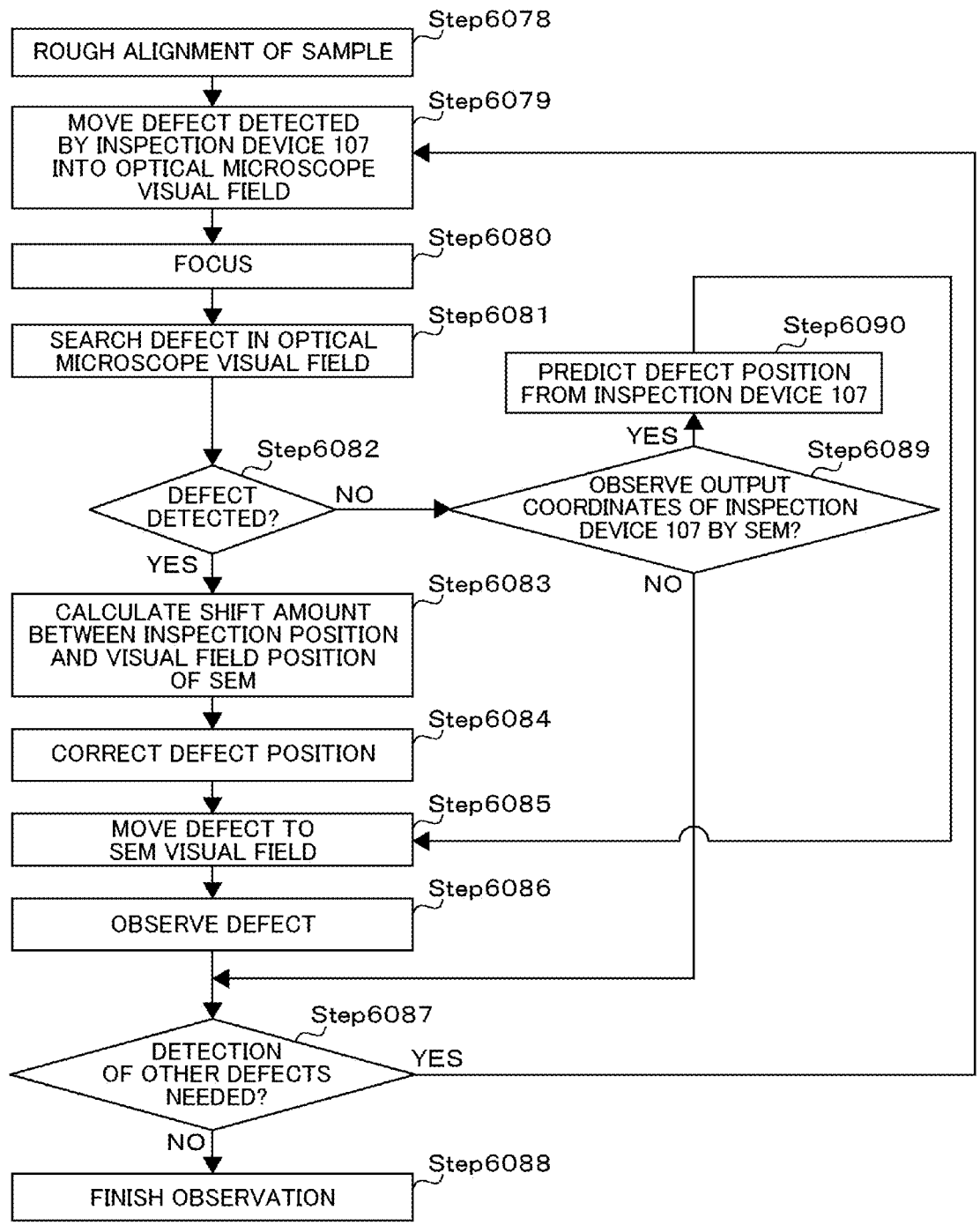
FIG. 17 is a flowchart of explaining an example of a procedure of observing a defect detected by an optical inspection device according to the second embodiment of the present invention.
Figure 18:
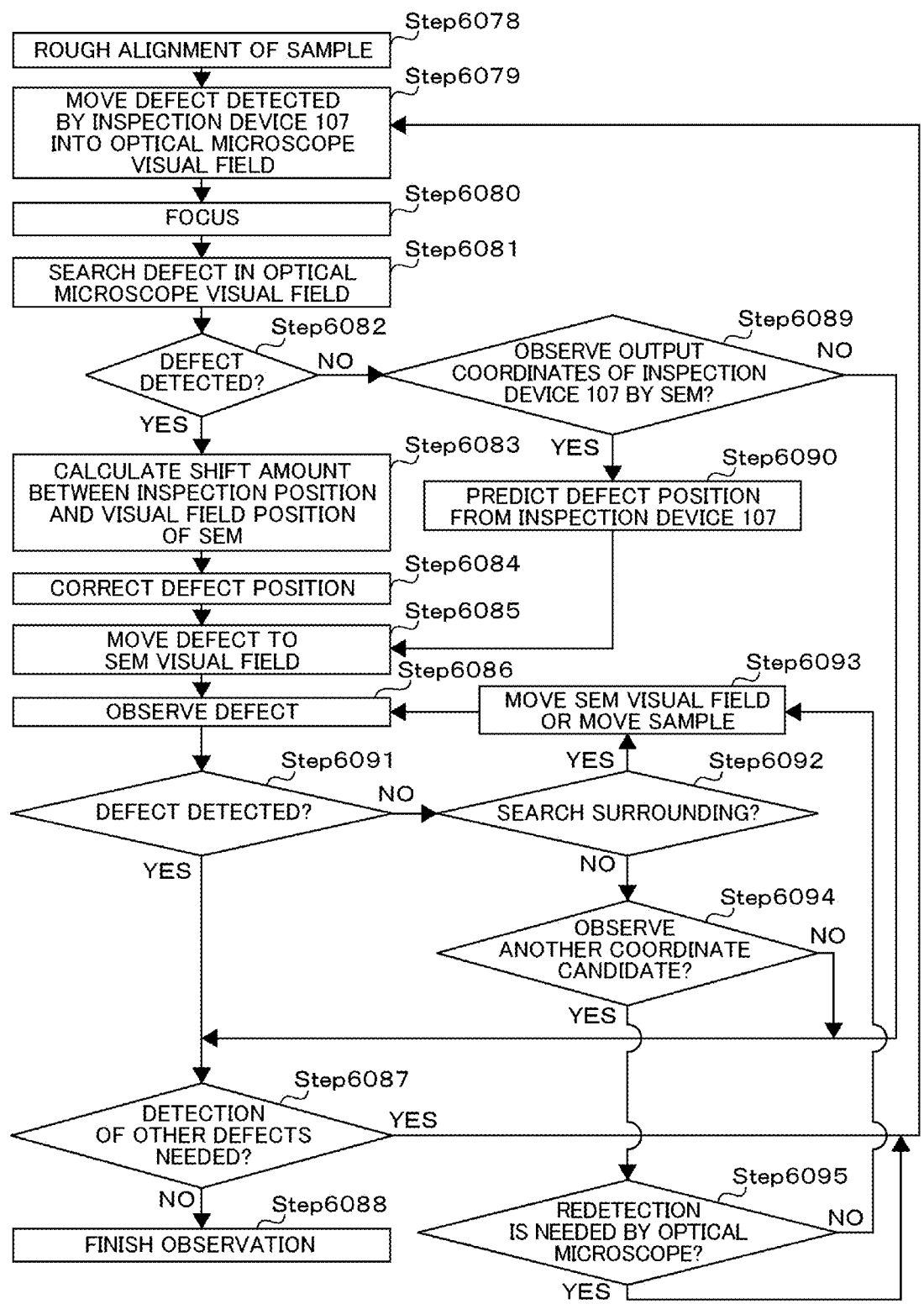
FIG. 18 is a flowchart of explaining an example of a procedure of observing a defect detected by an optical inspection device according to the second embodiment of the present invention.
Figure 19:
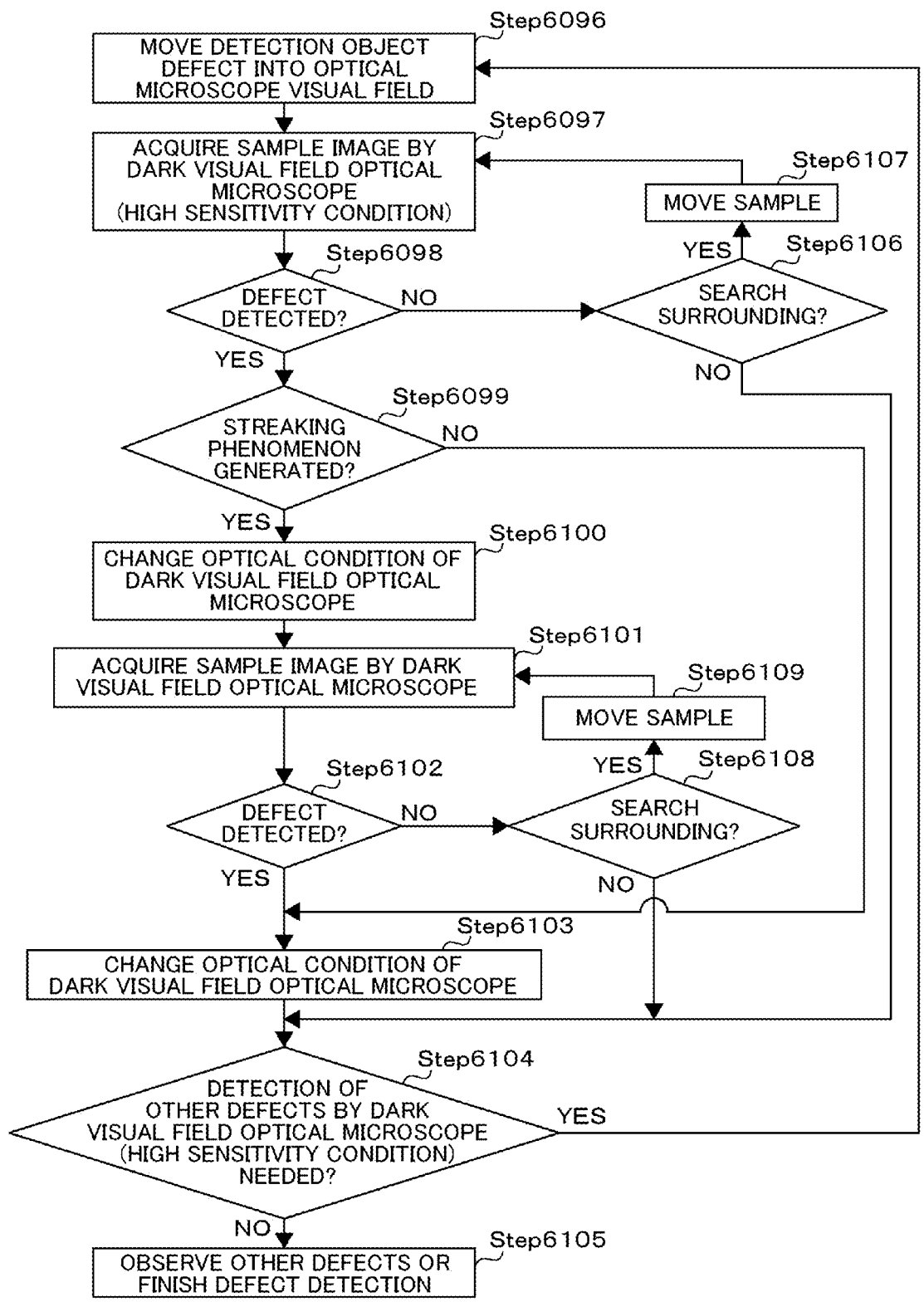
FIG. 19 is a flowchart of explaining an example of a procedure of observing a defect detected by an optical inspection device according to the second embodiment of the present invention.

Next, an explanation will be given of a flow of process observing the defect, which is detected by the other inspection device 107 (FIG. 10), by the review device 1000 explained by FIG. 10 in reference to FIG. 17, FIG. 18, and FIG. 19.

A description will be given of a process flow of FIG. 17. First, a defect on the sample 101 is detected by using the other inspection device 107, the inspection device 107 outputs inspection information of the sample 101 via the network 121, and inputs the inspection information to the storing device 124 of the review device 1000. Inspection information of the sample 101 outputted by the other inspection device 107 is inspection information configured by an inspection result configured by any of defect coordinates, a defect signal, a defect shape, polarization of defect scattered light, a defect kind, a defect label, a characteristic amount of a defect, and a scattered signal of a surface of the sample 101, or combinations of these, and an inspection condition configured by any of an illumination incidence angle, an illumination wavelength, an azimuth angle of illumination, an illumination intensity, and an illumination polarization of the other inspection device 107, an azimuth angle of a detecting unit, an elevation angle of the detecting unit, a detection region of the detecting unit or combinations of these. In a case where plural detectors are present in the other inspection device, there is used inspection information provided as a result of inspecting the sample 101 outputted for respective detectors or inspection information of the sample 101 synthesizing outputs of the plural detectors.

Next, a portion of defects or a total of defects extracted from defects detected by the other inspection device 107 are observed by the review device 1000 by using the information stored to the storing device 124. First, a rough alignment of the sample 101 is carried out (Step 6078). This is carried out by the bright visual field observation provided to the optical microscope 1052. Next, the stage 103 is moved so that a defect to be observed on the sample 101 falls within the visual field of the dark visual field observation by the optical microscope 1052 of the review device 1000 by using position information of the defect previously detected by the other inspection device 107 (Step 6079). Next, focusing is carried out by moving the objective lens 202 by the height control mechanism 209 (Step 6080).

Next, a defect is searched from an image acquired by taking the image by the dark visual field observation by the optical microscope 1052 (Step 6081), if the defect is detected (Step 6082—YES), a shift amount of a visual field position of the SEM 106 relative to the defect is calculated when the defect is going to be observed by the SEM 106 by using position information of the defect previously detected by the other inspection device 107 from a difference between a defect detecting position by the optical microscope 105 and position information of the defect previously detected by the other defect inspecting device (Step 6083). The position information of the defect previously detected by the other inspection device 107 is corrected based on the calculated shift amount (Step 6084), the defect the position information is corrected is moved to the visual field of the SEM 106 and the observation is carried out (Step 6086). At this time, the observed information is transmitted to the control system 125, and is registered to the database 122.

Incidentally, in a case there are a number of defects to be observed, representative several points thereamong are extracted, and a shift amount of a position of the defect detected previously by the other inspection device 107 and a visual field position of the SEM 106 from position information of the extracted defects previously detected by the other inspection device 107 and position information of respective defects provided by detecting by the dark visual field observation by the optical microscope 1052. By using the calculated shift amount, also with respect to defects other than the representative several points which are not detected by the dark visual field observation by the optical microscope 1052 or defects which cannot be detected by the dark visual field observation by the optical microscope 1052 (Step 6082—NO), position information provided by previously detecting by the other inspection device 107 is corrected (Step 6090), when needed (Step 6089—YES).

A description will be given of a process flow of FIG. 18. First, a defect on the sample 101 is detected by using the other inspection device 107, the other inspection device 107 outputs inspection information of the sample 101 via the network 121, to input it to the storing device 124 of the review device 1000. The inspection information of the sample 101 outputted by the other inspection device 107 is inspection information configured by an inspection result configured by any of defect coordinates, a defect signal, a defect shape, polarization of defect scattered light, a defect kind, a defect label, a characteristic amount of a defect, and a scattered signal of a surface of the sample 101, or combinations of these, and an inspection condition configured by any of an illumination incidence angle, an illumination wavelength, an azimuth angle of illumination, an illumination intensity, and an illumination polarization of the other inspection device 107, an azimuth angle of a detecting unit, an elevation angle of the detecting unit, a detecting region of the detecting unit, or combinations of these. In a case where there are plural detectors in the inspection device, inspection information provided as a result of inspecting the sample 101 outputted for each detector, or inspection information of the sample 101 synthesizing outputs plural detectors is used.

Next, a portion of defects, or a total of defects extracted from defects detected by the other inspection device 107 are observed by the review device 1000 by using information stored to the storing device 124. First, a rough alignment of the sample 101 is carried out (Step 6078). This is carried out by the bright visual field observation by the optical microscope 1052. Next, the stage 103 is moved such that a defect to be observed on the sample 101 falls within the visual field of the dark visual field observation by the optical microscope 1052 by using position information of the defect previously detected by the other inspection device 107 by the review device 1000 (Step 6079). Next, focusing is carried out by moving the objective lens 202 by the height control mechanism 209 (Step 6080).

Next, a defect is searched from an image acquired by taking the image by the dark visual field observation by the optical microscope 1052 (Step 6081). If the defect is detected (Step 6082—YES), a shift amount of a visual field position of the SEM 106 relative to the defect when the defect is going to be observed by the SEM 106 is calculated by using position information of the defect previously detected by the other inspection device 107 from a difference between a defect detecting position by the dark visual field observation by the optical microscope 1052 and position information of the defect detected previously by the other inspection device 107 (Step 6083). The position information of the defect previously detected by the other inspection device 107 is corrected based on the calculated shift amount (Step 6084), the defect the position information of which is corrected is moved to the visual field of the SEM 106, and the observation is carried out (Step 6086). At this time, observed information is transmitted to the control system 125 and registered to the database 122.

Incidentally, in a case where there are a number of defects to be observed, representative several points thereamong are extracted, a shift amount between a position of the defect previously detected by the other inspection device 107 and a visual field position of the SEM 106 is calculated from position information of the extracted defects previously detected by the other inspection device 107 and position information of respective defects provided by detecting by the dark visual field observation by the optical microscope 1052. By using information of the calculated shift amount, also with respect to defects other than the representative several points which cannot be detected by the dark visual field observation by the optical microscope 1052 or defects which cannot be detected by the dark visual field observation by the optical microscope 1052 (Step 6082—NO), position information provided by previously detecting by the other inspection device 107 is corrected (Step 6090), when needed (Step 6089—YES). Incidentally, in a case where the defect cannot be detected by the SEM 106 (Step 6091—NO) and the surrounding is searched by the SEM 106 (Step 6092—YES), the visual field of the SEM is moved or the surrounding is searched by moving the sample 101 (Step 6093), and the operation advances the process according to the procedure.

In a case where the defect cannot be detected by the SEM 106 (Step 6091—NO), the surrounding is not searched (Step 6092—NO), and other defect coordinate candidate is observed (Step 6094—YES), the defect is redetected by an optical condition which differs from the optical condition used at Step 6081 (Step 6095—YES) or, redetection is not carried out by the dark visual field observation by the optical microscope 1052 (Step 6095—NO), the image acquired at Step 6081 is used, a visual field of the SEM or the sample is moved to defect coordinates having a high possibility of presence of the defect other than the coordinates moved at Step 6085 (Step 6093), and the operation advances the process according to the procedure. The defect coordinates having the high possibility of the presence of the defect other than the coordinates moved at Step 6085 are derived by a method of using an image having accumulating time of the imaging element shorter than the accumulating time of the image used for deriving the defect coordinates at Step 6083 and having a small coordinates shift amount by elongating, or a method of deriving defect coordinates by using an algorithm different from an algorithm used for deriving the defect coordinates at Step 6083.

Next, an explanation will be given of a process flow of determining a elongating defect, or a non-elongating defect from an image acquired by the dark visual field observation by the optical microscope 1052, and deriving defect coordinates based on a result of the determination in reference to FIG. 19.

First, by the review device 1000, the stage 103 is moved so that a defect to be observed on the sample 101 falls within the visual field of the dark visual field observation by the optical microscope 1052 by using position information of the defect previously detected by the other inspection device 107 (Step 6096). Next, focusing is carried out by moving the objective lens 202 by the height control mechanism 209. Then, an image is acquired by taking the image by the dark visual field observation by the optical microscope 1052 (Step 6097). The defect is searched within the acquired image. If the defect is detected (Step 6098—YES), it is next determined whether the defect is the elongating defect or not from the image acquired at Step 6097. If the object defect is determined to be the elongating defect (Step 6099—YES), an optical condition of the dark visual field observation by the optical microscope 1052 is changed to an optical condition having a small influence of the elongating phenomenon (Step 6100). Then, the image is acquired by taking the image by the dark visual field observation by the optical microscope 1052 (Step 6101), and the defect is searched within the acquired image. And if the defect is detected (Step 6102—YES), the defect coordinates are derived from the image acquired at Step 6101 (Step 6103). Further, if the object defect is the non-elongating defect (Step 6099—NO), the defect coordinates are derived from the image acquired at Step 6097 (Step 6103).

Next, in a case that other defect information is needed at the dark visual field observation by the optical microscope 1052 (Step 6104—YES), defect position information to be observed is acquired from an output result of the other inspection device 107, the operation returns to a procedure of moving the defect to the dark visual field of the optical microscope 1052 set to the high sensitivity condition described above (Step 6096) and advances the process according to the procedure.

Incidentally, in a case where the defect cannot be detected from the image acquired at Step 6097 (Step 6098—NO), it is conceivable that the defect is present at outside of the visual field of the dark visual field observation by the optical microscope 1052, and therefore, a surrounding portion of the visual field of the dark visual field observation by the optical microscope 1052 may be searched. In a case of searching the surrounding portion (Step 6106—YES), the sample 101 is moved by an amount in correspondence with the visual field (Step 6107), and the operation advances the process according to the procedure from the defect detecting procedure described above. Further, in a case where the surrounding is not searched (Step 6106—NO), the operation advances the process according to the procedure.

Further, in a case where the defect cannot be detected from the image acquired at Step 6101 (Step 6102—NO), it is conceivable that the defect is present at outside of the visual field of the dark visual field observation by the optical microscope 1052, and therefore, the surrounding portion of the visual field of the dark visual field observation by the optical microscope 1052 may be searched. In a case of searching the surrounding portion (Step 6108—YES), the sample 101 is moved by an amount in correspondence with the visual field (Step 6109), and the operation advances the process according to the procedure from the defect detecting procedure described above. Further, in a case where the surrounding is not searched (Step 6108—NO), the operation advances the process according to the procedure.

Next, when it is not necessary to detect other defects by the dark visual field observation by the optical microscope 1052 (Step 6104—NO), the defect detection by the dark visual field observation by the optical microscope 1052 is finished (Step 6105). Incidentally, the optical condition changed at Step 6101 is the optical condition of any of an illumination light amount, an incidence angle of illumination, an azimuth angle of illumination, accumulating time in acquiring the image, an optical characteristic of the filter 205, or combinations of these. When the accumulating time of the image taking element 207 is shortened or the illumination light amount is reduced, a length of a tail of the elongating defect is shortened, and influence of the elongating phenomenon is reduced.

As a method of making illumination intensity variable, there are control of a voltage applied to the illumination optical system unit 201, an arrangement of an ND filter on an optical axis of the detection optical system, a switch of an optical path for changing an incidence angle of illumination and the like. Further, when the incidence angle of illumination or the azimuth angle of illumination is changed, a defect scattered light distribution is changed, and therefore, when an illumination azimuth is selected by which a region of strong intensity by locally concentrating defect scattered light and an aperture boundary of a detection optical system do not overlap each other, an influence of the elongating phenomenon can be suppressed.

As filters 205 used in an optical condition having less influence of the elongating phenomenon, there are an ND filter for reducing light, space filters for limiting apertures as shown in FIG. 8A and FIG. 8B, filters described in FIG. 6A and FIG. 6B and FIG. 7A and FIG. 7B and the like.

Although a specific explanation has been given of the invention carried out by the present inventors based on the embodiments as described above, the present invention is not limited to the embodiments, and naturally can be changed variously within the range not deviated from the gist.

REFERENCE SIGNS LIST

101 sample, 102 sample holder, 103 stage, 104 optical height detection system, 105 optical microscope, 106 electron microscope, 107 inspection device, 111 vacuum shielding window, 112 vacuum tank, 121 network, 122 database, 123 user interface, 124 storing device, 125 control system, 209 height control mechanism

The invention claimed is:

1. A defect detecting method comprising the steps of:
   irradiating a sample with a light from a light source of an illumination optical system arranged such that said light is incident on a surface of the sample from an oblique direction;
   condensing scattered light generated from the sample irradiated with the light and incident on an objective lens to focus an image of the scattered light;
   acquiring said image by using a controller to adjust a position of said objective lens with respect to the sample such that the focused image of the scattered light is focused onto a detection face of an imaging element;
   extracting a defect on the sample by processing the acquired image using a signal processor configured to calculate position information of the extracted defect; and
   outputting the calculated position information of the defect to a display,
   wherein in focusing the image of the scattered light, the controller is configured to suppress an occurrence of a elongating phenomenon by the scattered light scattered to a region near to an outer edge portion of an aperture of the objective lens by focusing a light partially shielding a component of the scattered light transmitting the region near to the outer edge portion of the aperture of the objective lens in the scattered light generated at the surface of the sample by irradiating the light in the scattered light incident on the objective lens, and wherein the position information of the extracted defect is calculated by the signal processor based on a luminance gravity center of the defect extracted from the image acquired by taking the image of the scattered light suppressing the occurrence of the elongating phenomenon by the scattered light scattered to the region near to the outer edge portion of the aperture of the objective lens.

2. The defect detecting method according to claim 1, wherein the scattered light incident on the objective lens is shielded in a shape of a concentric circle for a visual field of the objective lens.

3. The defect detecting method according to claim 1, wherein a portion of the region generating the scattered light scattered to the region near to the outer edge portion of the aperture of the objective lens is partially shielded for the aperture of the objective lens in the scattered light incident on the objective lens.

4. A defect detecting device comprising:

mounting stage which mounts a sample;

an illumination optical system which irradiates the sample by making a light incident on a surface of the sample mounted on the mounting stage from an oblique direction;

a focusing optical system including an objective lens which condenses a scattered light generated from the sample irradiated with the light by the illumination optical system, a focusing lens for focusing an image of the scattered light condensed by the objective lens, and an image taking element for taking an image of the scattered light focused by the focusing lens;

an image processor configured to extract a defect on the sample by processing an image of the scattered light provided by taking the image of the scattered light using the focusing optical system, and calculating position information of the extracted defect; and a display which outputs the position information of the defect calculated by the image processor, wherein the focusing optical system further includes a filter for partially shielding a scattered light scattered to a region near to an outer edge portion of an aperture of the objective lens in the scattered light incident on the objective lens, an image of the scattered light suppressing an occurrence of a elongating phenomenon by the scattered light scattered to the region near to the outer edge portion of the aperture of the objective lens is focused by focusing the scattered light transmitted through the filter by the focusing lens, and an image of the scattered light focused and suppressing the occurrence of the elongating phenomenon is taken by the image taking element, and wherein the image processor calculates the position information of the defect based on a luminance signal of the defect extracted from the image acquired by taking the image of the scattered light suppressing the occurrence of the elongating phenomenon.

5. The defect detecting device according to claim 4, wherein the filter shields the scattered light incident on the objective lens in a shape of a concentric circle for a visual field of the objective lens.

6. The defect detecting device according to claim 4, wherein the filter partially shields a portion of the region for generating the scattered light scattered to the region near to the outer edge portion of the objective lens for the aperture of the objective lens in the scattered light incident on the objective lens.

* * * * *